United States Patent
Korzheva et al.

(10) Patent No.: US 8,206,953 B2
(45) Date of Patent: Jun. 26, 2012

(54) MESSAGE ABUNDANCE AND ALLELE COPY NUMBER DETERMINATION USING IVT WITH SINGLE-STRANDED PRIMER-PROMOTER-SELECTOR CONSTRUCTS

(75) Inventors: Nataliya Korzheva, Somerville, NJ (US); Michael Seul, Fanwood, NJ (US)

(73) Assignee: BioArray Solutions, Ltd., Warren, NJ (US)

( * ) Notice: Subject to any disclaimer, the term of this patent is extended or adjusted under 35 U.S.C. 154(b) by 889 days.

(21) Appl. No.: 11/525,064

(22) Filed: Sep. 21, 2006

(65) Prior Publication Data

US 2007/0065864 A1    Mar. 22, 2007

Related U.S. Application Data

(60) Provisional application No. 60/719,063, filed on Sep. 21, 2005.

(51) Int. Cl.
*C12P 19/34* (2006.01)

(52) U.S. Cl. .................................. 435/91.21; 435/91.2

(58) Field of Classification Search ............... 435/91.21, 435/91.2
See application file for complete search history.

*Primary Examiner* — Gary Benzion
*Assistant Examiner* — Cynthia Wilder
(74) *Attorney, Agent, or Firm* — Womble Carlyle Sandridge & Rice LLP

(57) ABSTRACT

Disclosed is a single stranded primer-promoter-selector construct comprising (in 3' to 5' orientation) a primer subsequence annealing to the target, a T7 or other promoter subsequence (the template strand), and a selector subsequence. The primer can be extended by template mediated elongation, including reverse transcription, or ligation to another oligonucleotide. The promoter sequence is oriented to direct the in-vitro transcription (IVT) opposite to that of primer extension, where the selector subsequence serves as a template for IVT. The selector is associated with the target subsequence of interest and it, and the amplified product are unique subsequences, dissimilar to other sequence present in the sample. The construct's is useful for determination of the presence and relative abundance of designated subsequences in the sample, multiplex gene expression analysis, multiplex allele counting, determination of polymorphic/mutation site, and loss of heterozygosity.

17 Claims, 18 Drawing Sheets

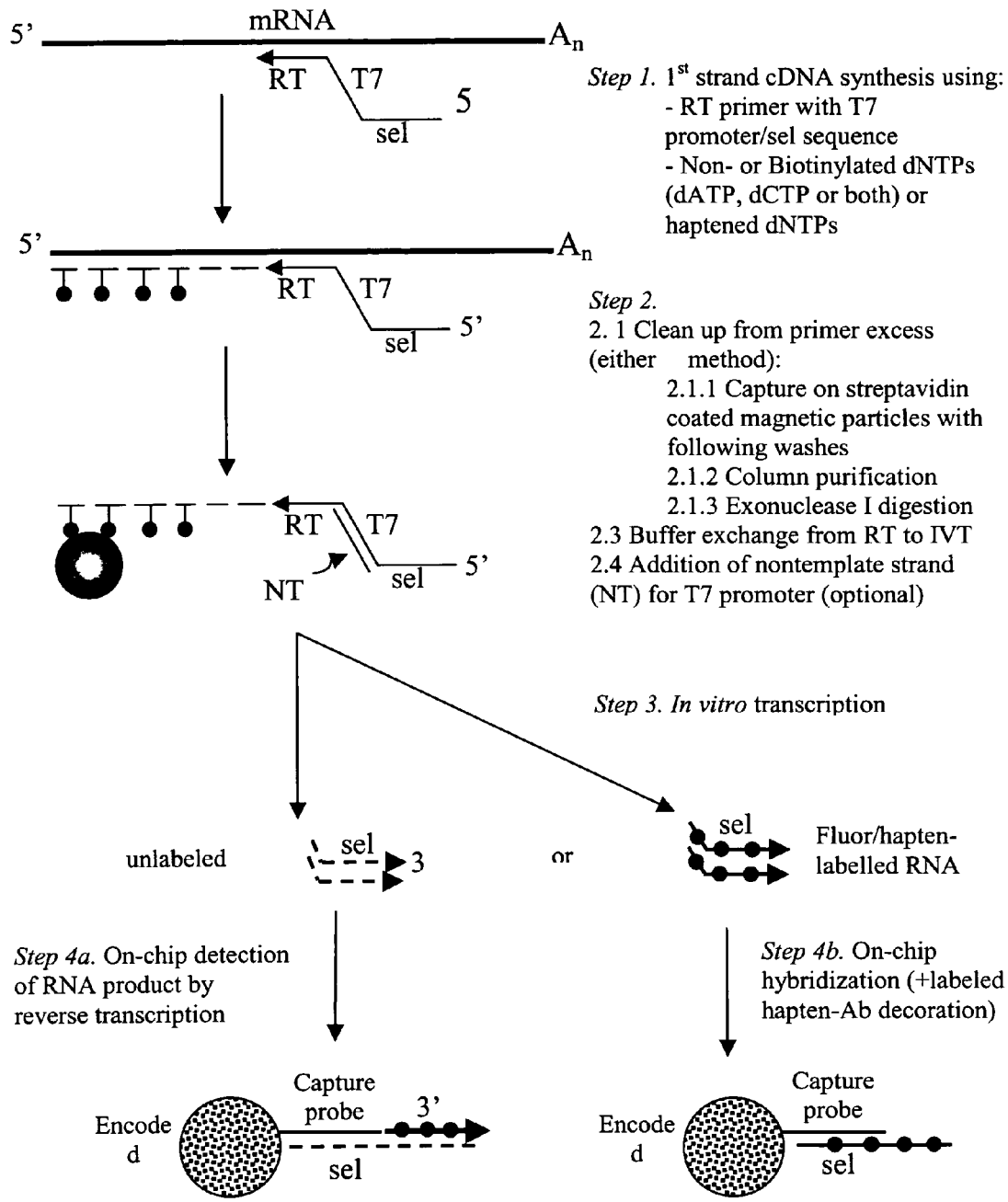
Fig. 2. Method for multiplexed genes expression analysis.

Method for SNP/mutation detection by allele-specific elongation

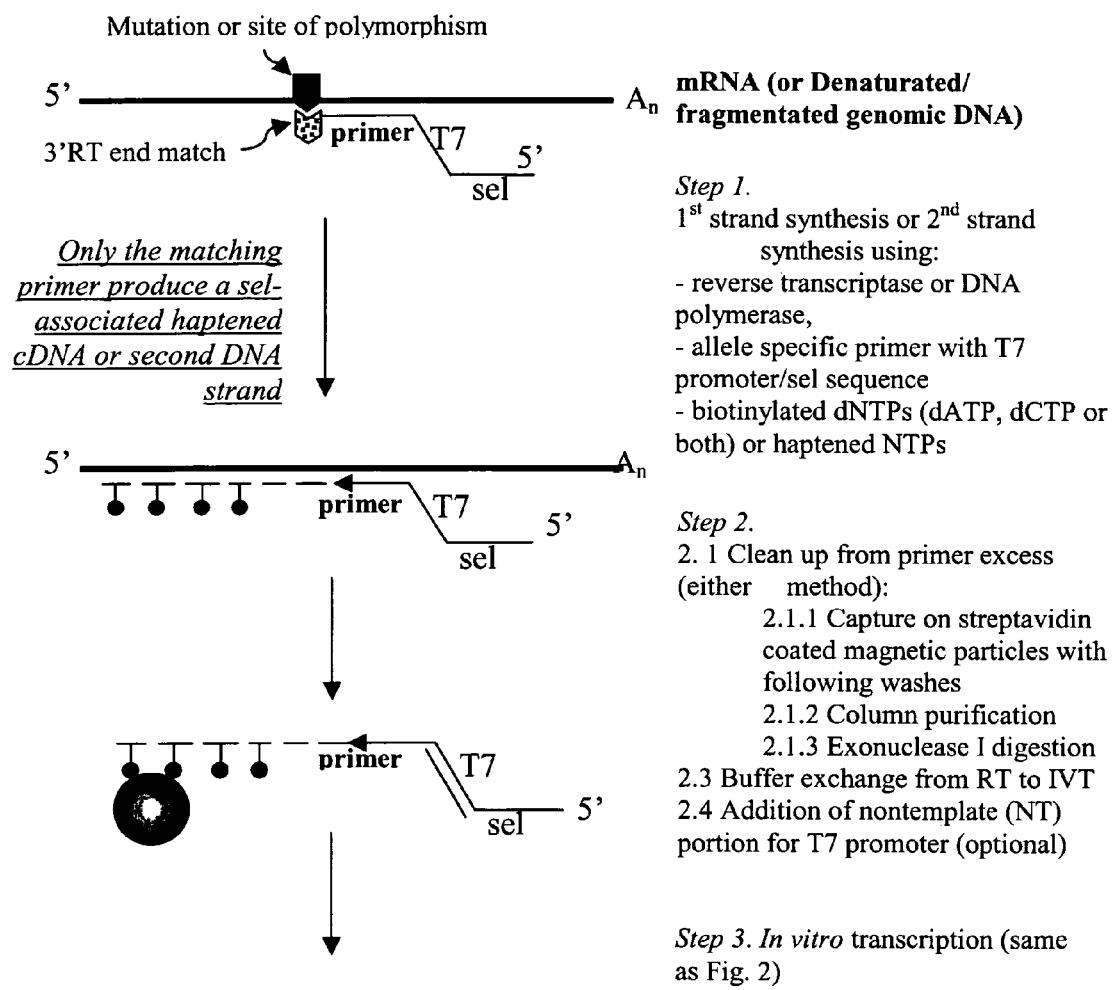

*Step 1.*
$1^{st}$ strand synthesis or $2^{nd}$ strand synthesis using:
- reverse transcriptase or DNA polymerase,
- allele specific primer with T7 promoter/sel sequence
- biotinylated dNTPs (dATP, dCTP or both) or haptened NTPs

*Step 2.*
2.1 Clean up from primer excess (either method):
    2.1.1 Capture on streptavidin coated magnetic particles with following washes
    2.1.2 Column purification
    2.1.3 Exonuclease I digestion
2.3 Buffer exchange from RT to IVT
2.4 Addition of nontemplate (NT) portion for T7 promoter (optional)

*Step 3.* In vitro transcription (same as Fig. 2)

*Step 4.* Allele-specific detection via sel sequences (same as Fig. 2, 4a and 4b)

Fig. 3

First version

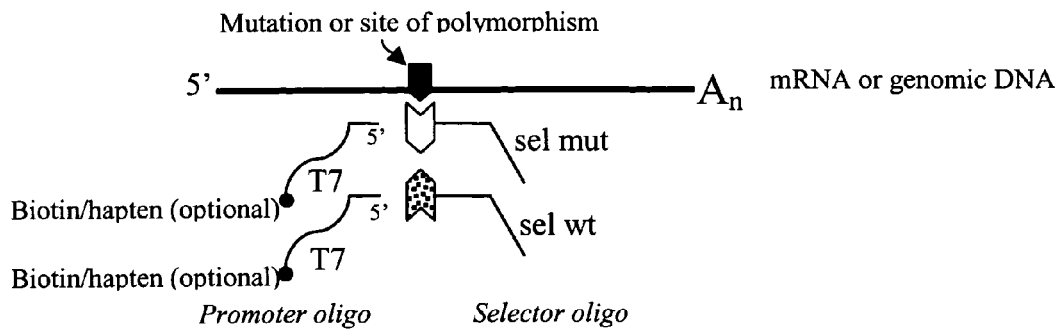

Second version

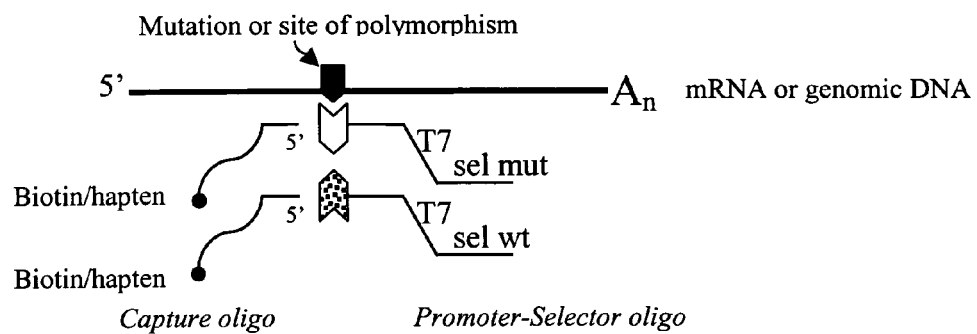

↓ Step 1. Hybridization of pair target-specific primers to the target

↓ Step 2. Ligation using mRNA or DNA as a template

↓ Step 3. Capture to streptavidin/Ab magnetic (or other) particle via biotin/hapten ↓ Step 4. Clean up of primers excess (first version may not require clean up step)

↓ Step 5. *In vitro* transcription (see Fig. 2)

↓ Step 6. Allele-specific detection via different sel sequences (see Fig. 2)

Fig. 4. Methods for SNP/mutation detection by allele-specific ligation.

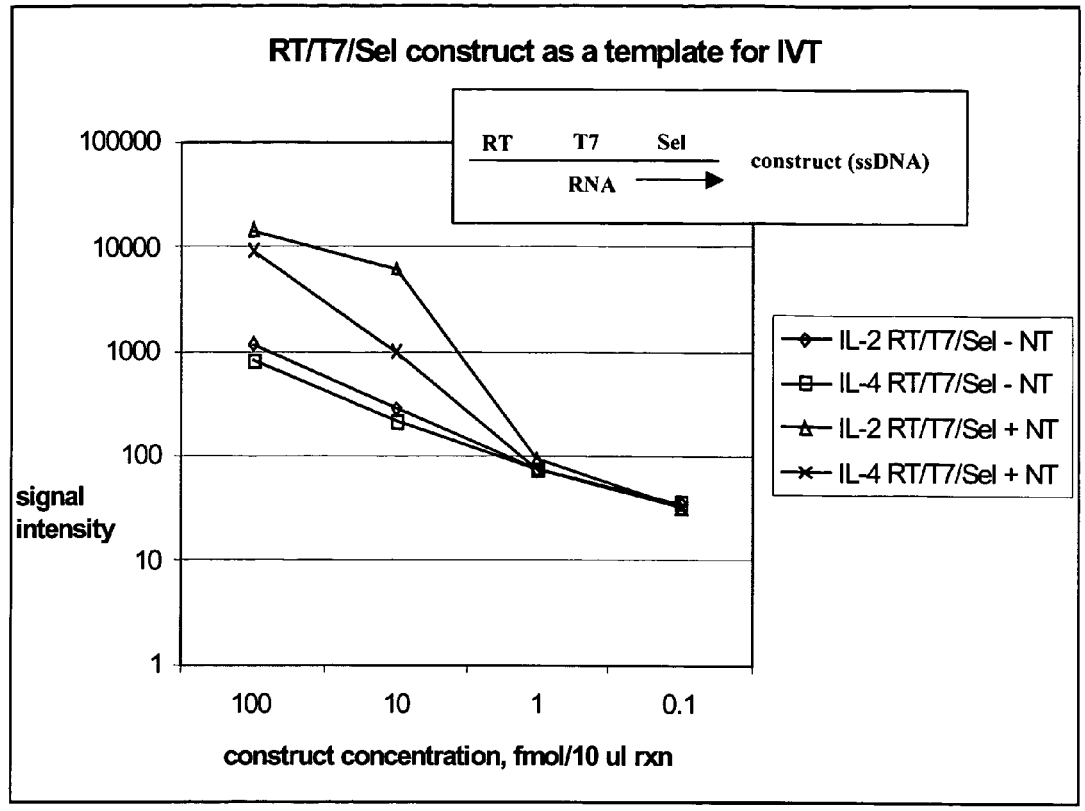

Oligo Sequences:

1) IL-2R RT/T7/Sel construct:
   5' GCA GGA TCC TGG TAT CCG CTA TCT CCC TAT AGT GAG TCG TAT TAA TTG GGC GTC AGA ATT GTCC [64 mer] [SEQ ID NO 1]
   Particle Capture probe IL-2R
   5'-amine- GCA GGA TCC TGG TAT CCG CTA [21 mer] [SEQ ID NO 2]

2) IL-4I RT/T7/Sel construct:
   5' GGA GTC AAC GGA TTT GGT CGT TCT CCC TAT AGT GAG TCG TAT TAG GAC GAG GAC GAG GAG GT [62 mer] [SEQ ID NO 3]
   Particle Capture probe IL-4I
   5'-amine- GGA GTC AAC GGA TTT GGT CGT [21 mer] [SEQ ID NO 4]

3) NT portion for T7 promoter:
   5' TAA TAC GAC TCA CTA TAG GGA GA [23 mer] [SEQ ID NO 5]

Fig. 5. Characterization of sequence-specificity and concentration dependence of sst-IVT reaction.

*Oligo Sequences:*
1) Kan RT/T7/Sel construct:
   5' GCA GGA TCC TGG TAT CCG CTA TCT CCC TAT AGT GAG TCG TAT TACTGAATCCGGTGAGAATGGC [64 mer] [SEQ ID NO 6]

2) Particle Capture probe
   5'-amine- GCA GGA TCC TGG TAT CCG CTA [21 mer] [SEQ ID NO 7]

3) NT portion for T7 promoter:
   5' TAA TAC GAC TCA CTA TAG GGA GA [23 mer] [SEQ ID NO 8]

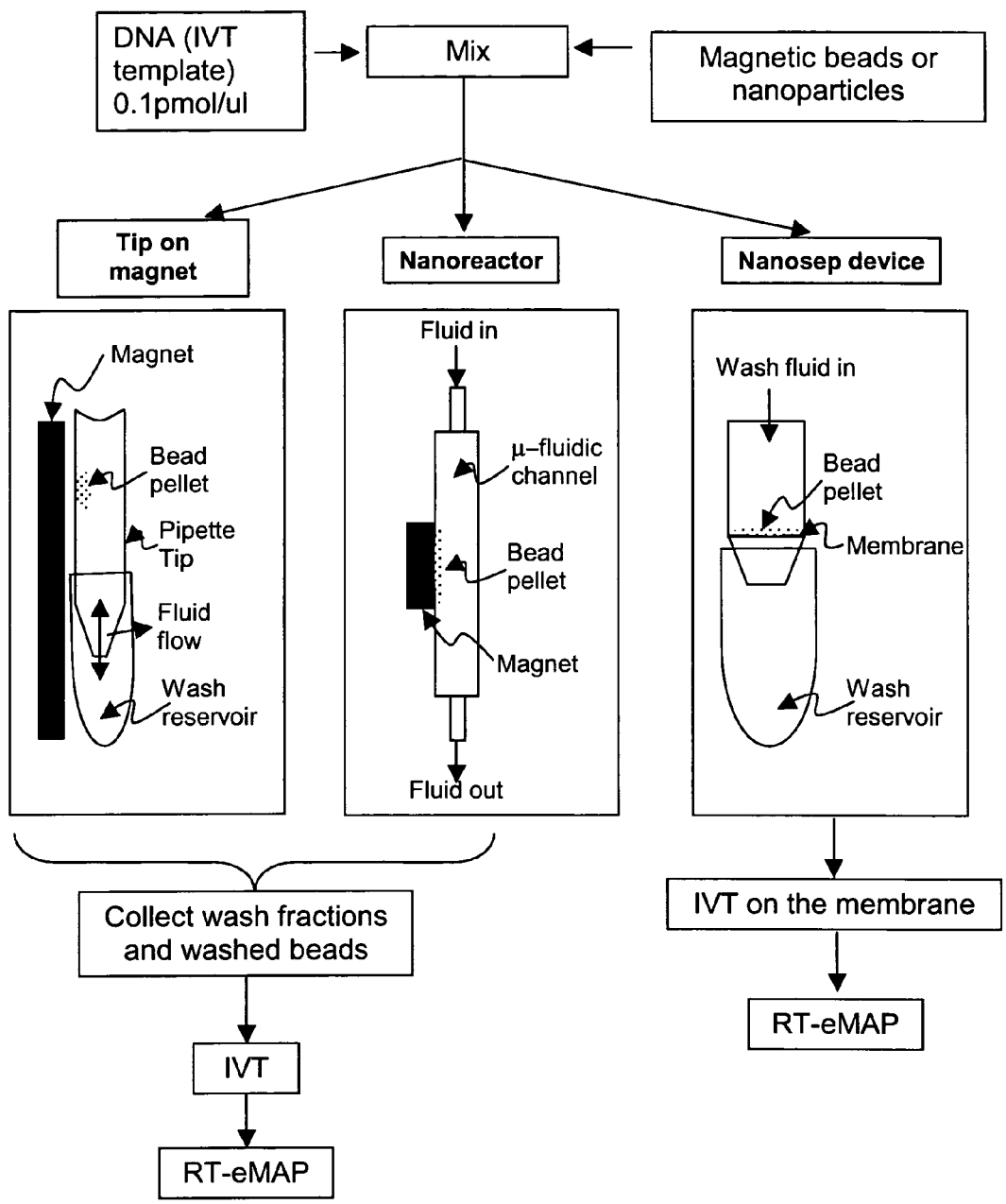
Fig. 9. Clean up configurations with magnetic capture and flow-through separation.

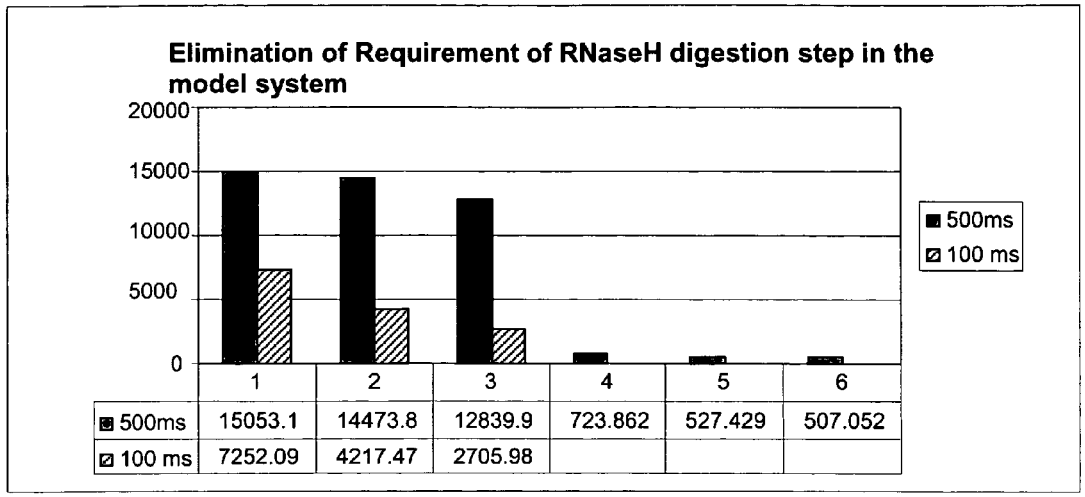

*Efficiency sst-IVT using template in different configurations.* 1 and 4: construct (RT primer) only; 2 and 5: construct annealed to RNA; 3 and 6: construct annealed to RNA and digested with RNaseH; the NT portion of the T7 promoter was added in reactions 1, 2 and 3, and was omitted in the reactions 4, 5 and 6. Exposure times of respectively 500 ms and 100 ms were used to record assay images for the two data sets, as shown.

IL-2R RT/T7/Sel primer:
    5' GCA GGA TCC TGG TAT CCG CTA TCT CCC TAT AGT GAG TCG TAT TAA
    TTG GGC GTC AGA ATT GTCC [64 mer] [SEQ ID NO 9]
    Particle Capture probe IL-2-R
    5'-amine- GCA GGA TCC TGG TAT CCG CTA [21 mer] [SEQ ID NO 10]

Il-2 RNA
    5' CGA CAA UUC UGA CGC CCA AUG GGA AUG AAG ACA CCA CAG CUG AUU
    UCU UC [50 mer] [SEQ ID NO 11]

Fig. 10

Fig. 14. Closely homologous sequences from the zein gene family (*azs 22*) of Maize.

Nucleotide polymorphism for 7 expressed genes in the inbred line BSSS53

```
05 ATAATATTTTGAGCATTCAGAAACACACCAAGCGAAGCACATTAGCAACAACCTAACAAC 60
22 ATAATATTTTGAGCATTCAGAAACACACCAAGCGAAGCGCACTAGCAACAACCTAACAAC
16 ATAATACTTTGAGCATTCAGAAACACACCAAGCGAAGCGCACTAGCAACGACCAAACAAC
31 ATAATATTTTGAGCATTCAGAAACACACCAAGCGAAGCGCACTAGCAACGACCAAACAAC
12 ATAATATTTTGAGCATTCAGAAACACACCAAGCGAAGCTACCTAGCAACGACTTAACAAC
32 ATAATATTTTGAGCATTCAAAAACACACCAAGCGAAGCTCACTAGCAACGACCTAACAAC
24 ATAATATTTTCAGCATTCAAAAACACACCAAGCGAAGCGCACTAGCAACGACCTAACACC
   ****** *** ******* ****************   ********  ** **** *

05 AATGGCTACCAAGATATTATCCCTCCTTGCGCTTCTTGCGCTTTTTGCGAGCGCAACAAA 120
22 AATGGCTACCAAGATATTATCCCTCCTTGCGCTTCTTGCGCTTTTTGCGAGCGCAACAAA
16 AATGGCTACCAAGATATTAGCCCTCCTTGCGCTTCTTGCCCTTTTTGTGAGCGCAACAAA
31 AATGGCTACCAAGATATTAGCCCTCCTTGCGCTTCTTGCCCTTTTTGTGAGCGCAACAAA
12 AATGGCTACCAAGATATTAGCCCTCCTTGCGCTTCTTGCCCTTTTTGTGAGCGCAACAAA
32 AATGGCTACCAAGATATTAGCCCTCCTTGCGCTTCTTGCCCTTTTTGTGAGCGCAACAAA
24 AATGGCTACCAAGATATTAGCCCTCCTTGCGCTTCTTGCCCTTTTAGTGAGCGCAACAAA
   ******************  ******************  ***** * ***********

05 TGCGTTCATTATTCCACAATGCTCACTTGCTCCAAGTTCCATTATTACACAGTTCCTCCC 180
22 TGCGTCCATTATTCCACAATGCTCACTTGCTCCTAGTTCCATTATTCCACAGTTCCTCCC
16 TGCGTTCATTATTCCACAATGCTCACTTGCTCCTAGTGCCATTATTCCACAGTTCCTCCC
31 TGCGTTCATTATTCCACAATGCTCACTTGCTCCTAGTGCCATTATTCCACAGTTCCTCCC
12 TGCGTTCATTATTCCACAATGCTCACTTGCTCCTAGTGCCATTATACCACAGTTCCTCCG
32 TGCGTTCATTATTCCACAATGCTCACTTGCTCCTAGTGCCATTATTCCACAGTTCCTCCC
24 TGCGTTCATTATTCCACAGTGCTCACTTGCTCCTAGTGCCAGTATTCCACAGTTCCTCCC
   ***** ************ ***************  *** *** ***  **********

05 ACCAGTTACTTCAATGGGCTTCGAACACCCAGCTGTGCAAGCCTATAGGCTACAACAAGC 240
22 ACCAGTTACTTCAATGGCCTTCGAACACCCAGCTGTGCAAGCCTATAGGCTACAACAAGC
16 ACCAGTTACTTCAATGGGCTTCGAACACTCAGCTGTGCAAGCCAACAGGCTACAACAAGC
31 ACCAGTTACTTCAATGGGCTTCGAACACTCAGCTCTGCAAGCCAACAGGCTACAACAAGC
12 ACCAGTTACTTCAATGGGCTTCGAACACCTAGCTGTGCAAGCCTACAAGCTACAACAAGC
32 ACCAGTTACTTCAATGGGCTTCGAACACCTAGCTGTGCAAGCCTACAGGCTACAACAAGC
24 ACCAGTTACTTCAATGGGCTTCGAACATCCAGCCGTGCAAGCCTACAGGCTACAACTAGC
   *****************  ********    ***   ********  *  ******* ***

05 AATTGCGGCGAGCGTCTTACAACAACCAATTTCCCAGTTGCAACAACAATCCTTGGCACA 300  SEQ ID NO 12
22 GATTGCGGCGAGCGTCTTACAACAACCAATTGCCCAATTGCAACAACAATCCTTGGCACA      SEQ ID NO 13
16 GCTTGCGGCGAGCGTCTTACAACAACCAATTGCCCAATTGCAACAACAATCTTTGGCACA      SEQ ID NO 14
31 GCTTGCGGCGAGCGTCTTACAACAACCAATTGCCCAATTGCAACAACAATCTTTGGCACA      SEQ ID NO 15
12 GCTTGCGGCGAGCGTCTTACAACAACCAATTAACCAATTGCAACAACAATCCTTGGCACA      SEQ ID NO 16
32 GCTTACGGCGAGCGTCTTACAACAACCAATTGACCAA-------------------          SEQ ID NO 17
24 GCTTGCGGCGAGCGCCTTACAACAACCAATTGCCCAATTGCAACAACAATCCTTGGCACA      SEQ ID NO 18
   **  ******** **************** *   ***
```

Fig. 16. Coassembled bead array.

SEQUENCE LISTING

<160> NUMBER OF SEQ ID NOS: 18

<210> SEQ ID NO 1
<211> LENGTH: 64
<212> TYPE: DNA
<213> ORGANISM: Artificial Sequence
<220> FEATURE:
<223> OTHER INFORMATION: Artificial Primer

<400> SEQUENCE: 1
gcaggatcct ggtatccgct atctccctat agtgagtcgt attaattggg cgtcagaatt    60
gtcc                                                                 64

<210> SEQ ID NO 2
<211> LENGTH: 21
<212> TYPE: DNA
<213> ORGANISM: Artificial Sequence
<220> FEATURE:
<223> OTHER INFORMATION: Artificial Probe

<400> SEQUENCE: 2
gcaggatcct ggtatccgct a                                              21

<210> SEQ ID NO 3
<211> LENGTH: 62
<212> TYPE: DNA
<213> ORGANISM: Artificial Sequence
<220> FEATURE:
<223> OTHER INFORMATION: Artificial Primer

<400> SEQUENCE: 3
ggagtcaacg gatttggtcg ttctccctat agtgagtcgt attaggacga ggacgaggag    60
gt                                                                   62

<210> SEQ ID NO 4
<211> LENGTH: 21
<212> TYPE: DNA
<213> ORGANISM: Artificial Sequence
<220> FEATURE:
<223> OTHER INFORMATION: Artificial Probe

<400> SEQUENCE: 4
ggagtcaacg gatttggtcg t                                              21

<210> SEQ ID NO 5
<211> LENGTH: 23
<212> TYPE: DNA
<213> ORGANISM: Artificial Sequence
<220> FEATURE:
<223> OTHER INFORMATION: Artificial Promoter

<400> SEQUENCE: 5
taatacgact cactataggg aga                                            23

<210> SEQ ID NO 6
<211> LENGTH: 64
<212> TYPE: DNA
<213> ORGANISM: Artificial Sequence
<220> FEATURE:
<223> OTHER INFORMATION: Artificial Primer -continued

<400> SEQUENCE: 6
gcaggatcct ggtatccgct atctccctat agtgagtcgt attactgaat ccggtgagaa    60
tggc    64

<210> SEQ ID NO 7
<211> LENGTH: 21
<212> TYPE: DNA
<213> ORGANISM: Artificial Sequence
<220> FEATURE:
<223> OTHER INFORMATION: Artificial Probe

<400> SEQUENCE: 7
gcaggatcct ggtatccgct a    21

<210> SEQ ID NO 8
<211> LENGTH: 23
<212> TYPE: DNA
<213> ORGANISM: Artificial Sequence
<220> FEATURE:
<223> OTHER INFORMATION: Artificial Promoter

<400> SEQUENCE: 8
taatacgact cactataggg aga    23

<210> SEQ ID NO 9
<211> LENGTH: 64
<212> TYPE: DNA
<213> ORGANISM: Artificial Sequence
<220> FEATURE:
<223> OTHER INFORMATION: Artificial Primer

<400> SEQUENCE: 9
gcaggatcct ggtatccgct atctccctat agtgagtcgt attaattggg cgtcagaatt    60
gtcc    64

<210> SEQ ID NO 10
<211> LENGTH: 21
<212> TYPE: DNA
<213> ORGANISM: Artificial Sequence
<220> FEATURE:
<223> OTHER INFORMATION: Artificial Probe

<400> SEQUENCE: 10
gcaggatcct ggtatccgct a    21

<210> SEQ ID NO 11
<211> LENGTH: 50
<212> TYPE: RNA
<213> ORGANISM: Artificial Sequence
<220> FEATURE:
<223> OTHER INFORMATION: Artificial RNA

<400> SEQUENCE: 11
cgacaauucu gacgcccaau gggaaugaag acaccacagc ugauuucuuc    50

<210> SEQ ID NO 12
<211> LENGTH: 300
<212> TYPE: DNA
<213> ORGANISM: Maize

<400> SEQUENCE: 12
ataatatttt gagcattcag aaacacacca agcgaagcac attagcaaca acctaacaac    60
aatggctacc aagatattat ccctccttgc gcttcttgcg cttttttgcga gcgcaacaaa   120

-continued

```
tgcgttcatt attccacaat gctcacttgc tccaagttcc attattacac agttcctccc      180
accagttact tcaatgggct tcgaacaccc agctgtgcaa gcctataggc tacaacaagc      240
aattgcggcg agcgtcttac aacaaccaat ttcccagttg caacaacaat ccttggcaca      300
```

<210> SEQ ID NO 13
<211> LENGTH: 300
<212> TYPE: DNA
<213> ORGANISM: Maize

<400> SEQUENCE: 13

```
ataatatttt gagcattcag aaacacacca agcgaagcgc actagcaaca acctaacaac       60
aatggctacc aagatattat ccctccttgc gcttcttgcg cttttttgcga gcgcaacaaa      120 tgcgtccatt attccacaat gctcacttgc tcctagttcc attattccac agttcctccc      180
accagttact tcaatggcct tcgaacaccc agctgtgcaa gcctataggc tacaacaagc      240
gattgcggcg agcgtcttac aacaaccaat tgcccaattg caacaacaat ccttggcaca      300
```

<210> SEQ ID NO 14
<211> LENGTH: 300
<212> TYPE: DNA
<213> ORGANISM: Maize

<400> SEQUENCE: 14

```
ataatacttt gagcattcag aaacacacca agcgaagcgc actagcaacg accaaacaac       60
aatggctacc aagatattag ccctccttgc gcttcttgcc cttttttgtga gcgcaacaaa      120 tgcgttcatt attccacaat gctcacttgc tcctagtgcc attattccac agttcctccc      180
accagttact tcaatgggct tcgaacactc agctgtgcaa gccaacaggc tacaacaagc      240
gcttgcggcg agcgtcttac aacaaccaat tgcccaattg caacaacaat ctttggcaca      300
```

<210> SEQ ID NO 15
<211> LENGTH: 300
<212> TYPE: DNA
<213> ORGANISM: Maize

<400> SEQUENCE: 15

```
ataatatttt gagcattcag aaacacacca agcgaagcgc actagcaacg accaaacaac       60
aatggctacc aagatattag ccctccttgc gcttcttgcc cttttttgtga gcgcaacaaa      120 tgcgttcatt attccacaat gctcacttgc tcctagtgcc attattccac agttcctccc      180
accagttact tcaatgggct tcgaacactc agctctgcaa gccaacaggc tacaacaagc      240
gcttgcggcg agcgtcttac aacaaccaat tgcccaattg caacaacaat ctttggcaca      300
```

<210> SEQ ID NO 16
<211> LENGTH: 300
<212> TYPE: DNA
<213> ORGANISM: Maize

<400> SEQUENCE: 16

```
ataatatttt gagcattcag aaacacacca agcgaagcta cctagcaacg acttaacaac       60
aatggctacc aagatattag ccctccttgc gcttcttgcc cttttttgtga gcgcaacaaa      120 tgcgttcatt attccacaat gctcacttgc tcctagtgcc attataccac agttcctccg      180
accagttact tcaatgggct tcgaacacct agctgtgcaa gcctacaagc tacaacaagc      240
gcttgcggcg agcgtcttac aacaaccaat taaccaattg caacaacaat ccttggcaca      300
```

```
<210> SEQ ID NO 17
<211> LENGTH: 277
<212> TYPE: DNA
<213> ORGANISM: Maize

<400> SEQUENCE: 17
ataatatttt gagcattcaa aaacacacca agcgaagctc actagcaacg acctaacaac      60
aatggctacc aagatattag ccctccttgc gcttcttgcc cttttttgtga gcgcaacaaa    120 tgcgttcatt attccacaat gctcacttgc tcctagtgcc attattccac agttcctccc    180
accagttact tcaatgggct tcgaacacct agctgtgcaa gcctacaggc tacaacaagc    240
gcttacggcg agcgtcttac aacaaccaat tgaccaa                              277

<210> SEQ ID NO 18
<211> LENGTH: 300
<212> TYPE: DNA
<213> ORGANISM: Maize

<400> SEQUENCE: 18
ataatatttt cagcattcaa aaacacacca agcgaagcgc actagcaacg acctaacacc      60
aatggctacc aagatattag ccctccttgc gcttcttgcc cttttagtga gcgcaacaaa    120
tgcgttcatt attccacagt gctcacttgc tcctagtgcc agtattccac agttcctccc    180
accagttact tcaatgggct tcgaacatcc agccgtgcaa gcctacaggc tacaactagc    240
gcttgcggcg agcgccttac aacaaccaat tgcccaattg caacaacaat ccttggcaca    300
```

MESSAGE ABUNDANCE AND ALLELE COPY NUMBER DETERMINATION USING IVT WITH SINGLE-STRANDED PRIMER-PROMOTER-SELECTOR CONSTRUCTS

RELATED APPLICATIONS

This application claims priority to U.S. Provisional No. 60/719,063, filed Sep. 21, 2005.

STATEMENT OF POTENTIAL GOVERNMENT INTEREST

The invention was developed in part with funding from SBIR Grant No. DAMD17-03-C-0047 C under a program administered by U.S. Army. The government may have rights in the invention.

BACKGROUND

Linear amplification of mRNA or genomic DNA using in vitro transcription, or IVT, is a well-known method of molecular biology (see Krieg & Melton, 1984, Melton, 1984). Because IVT, for each target, produces a number of RNA products that is proportional to the original number of copies of that target, it permits the determination of relative message abundance (U.S. Pat. Nos. 5,545,522; 5,716,785; and 5,891,636; Van Gelder et al, 1990) and thus has been widely applied in the context of gene expression analysis (U.S. Pat. No. 5,514,545). IVT also is a central element in certain isothermal methods of exponential target amplification which are capable of detecting pathogen RNA or mRNA at low levels (U.S. Pat. No. 5,399,491; European Patent No. 0 368 906 B2; Guatelli et al., 1990).

In accordance with prior art, as disclosed in U.S. Pat. Nos. 6,291,170 and 5,514,545, as well as in U.S. Patent Applications 2005/0130194 and 2005/0123943, the conventional sequence of step is as follows: cDNA synthesis is performed, most frequently using a primer complementary to polyA 3'-end of RNA which includes a T7 promoter sequence (non-template strand) at its 5'-end; alternatively, sequence or gene-specific primers may be placed in positions other than the 5'-end. After RNaseH digestion of the RNA template or heat denaturation of RNA-DNA hybrid, second strand DNA synthesis is performed (Goubler, U., 1983), to produce dsDNA of full or partial length (depending on primer placement), incorporating a double-stranded T7 promoter sequence (and adjacent regions). In practical realizations of the method, DNA polymerase or RT must be added to the reaction to effectively catalyze second strand synthesis (see U.S. Pat. No. 5,545,522, describing use of *E. Coli* DNA Polymerase; Kwoh et al., 1989). Antisense RNA (aRNA) is synthesized from the second strand of DNA by in-vitro transcription, and the aRNA products are detected, for example by hybridization to capture oligonucleotide probes, including variants such as molecular beacons (Vet, J. A. M., 2002; see also BioArray Solutions patent application Ser. No. 11/218,838; filed Sep. 2, 2005, below) or the hybridization protection assay (see U.S. Pat. No. 6,004,745; Arnold et al.), or probe elongation. All these methods of the art require the synthesis of double-stranded cDNA from the original mRNA targets, and the intervening step of RNA degradation. The complex and time-consuming steps of these methods have effectively confined them to the laboratory research. In a clinical setting, the use of such complex protocols would require special training, and often certification, of technical staff in laboratories qualified to conduct such complex ("esoteric") analysis.

Nucleic Acid Detection and Sequence Analysis—IVT also can be applied to DNA analysis, including mutation or polymorphism analysis. Generally, these applications require exponential amplification of genetic material i.e., genomic DNA, most commonly by application of the polymerase chain reaction (Syvanen, A. C., 2005, see, e.g., U.S. Pat. No. 4,683,202; Mullis) or whole genome amplification, in a multiplicity of variants (see, e.g. USCD patents on ligation-mediated whole genome amplification U.S. Pat. No. 5,686,243). IVT offers a method of strand selection following PCR amplification (see, e.g., BioArray Solutions Application filed Sep. 2, 2005; Ser. No. 11/218,838; filed (IVT)) which, inter alia, has the advantage of permitting the combination of that step with subsequent multiplexed detection of RNA strands produced in the IVT reaction.

It will be useful to simplify and accelerate the design of reliable multiplexed amplification and detection reactions, and to replace the complex procedures for gene expression analysis (U.S. Pat. No. 5,514,545) and other tasks of nucleic acid analysis by simpler, more robust protocols suitable for the clinical setting. Especially in that context, it also will be useful to develop integrated protocols, that is, protocols which combine multiple steps of analysis, preferably in a manner permitting the realization of homogeneous assay formats. It will be especially useful, in order to reduce the time required for assay completion, and particularly "hands-on" time, to combine amplification and analysis, by detection of multiple amplification products. Further, the combination of steps, preferably in a manner compatible with the realization of homogeneous assay formats, will facilitate miniaturization, which in turn will to reduce the consumption of reagents as well as the risk of contamination, both of samples and of laboratory facilities.

An IVT reaction—and in particular, an IVT reaction using a single-stranded template (rather than a double-stranded template), as described herein—offers many of these advantages.

In fact, the ability of the T7 RNA polymerase to utilize the template strand of the promoter in single-stranded form, and catalyze transcription from a single-stranded template (sst) producing a copy of the parent DNA strand of interest, has been described in the literature (Kukarin, A. et al, 2003; Korencic D. et al, 2002; Temiakov D. et al, 2002). However, in practical implementations of (conventional) IVT, this reaction has been regarded as an adverse side effect of in-vitro transcription.

The sst-IVT reaction, to date, has not been fully applied to the development and realization of complex analytical protocols, primarily because of certain generally undesirable characteristics. First, its modest yield—compared to the regular IVT format using double-stranded (ds) DNA templates—limits the sensitivity of assay protocols performed in conventional configurations that require a substantial number of target molecule; and its poor performance in buffers of even modest ionic strength generally renders it incompatible with other upstream and downstream enzymatic reactions employed in existing assay protocols. However, by addressing these points as described below, sst-IVT can be optimized to make it suitable for numerous applications of nucleic acid analysis, in a manner permitting the integration of amplification and concurrent detection and analysis of multiple products.

BACKGROUND REFERENCES (ALL INCORPORATED BY REFERENCE)

The following can be referred to as background in order to aid in understanding of certain of the terms and expressions below. These references are sometimes referred to in the text below by author, number, or other designation.

Seo, M. Y., Rha, S. Y., Yang S. H., Kim, S. C., Lee, G. Y., Park, C. H., Chung, H. C. et al. 2004. The pattern of gene copy number changes in bilateral breast cancer surveyed by cDNA microarray-based comparative genomic hybridization. *Int. J. of Mol Med* 13: 17-24

Sellers, W. R. 2005. Nature, July 7 issue

Hirsch F. R. et al. 2005. *J Natl Cancer Inst* 97:621-623, 643-655.

Ogino S. Wilson R B., 2004. pinal muscular atrophy: molecular genetics and diagnostics. Expert Rev Mol Diagn. 2004 January; 4(1):15-29.

Dutta S. Nandagopal K, Gangopadhyay P K, Mukhopadhyay K., 2005. Molecular aspects of down syndrome. Indian Pediatr. 2005 April; 42(4):339-44.

Gubler, U., and Hoffman, B. (1983) *Gene* 25, 263-269

Vet, Jacqueline A. M., Van der Rijt J. M., and Blom Henk J. 2002. Molecular beacons: colorful analysis of nucleic acids. *Expert Rev. Mol. Diagn* 2(1)

Kukarin A., Rong M, McAllister W T. 2003. Exposure of T7 RNA polymerase to the isolated binding region of the promoter allows transcription from a single-stranded template. *J Biol Chem.* 278(4):2419-24

Korencic D, Soll D, Ambrogelly A. 2002. A one-step method for in-vitro production of tRNA transcripts. *Nucleic Acids Res.* 30(20):e105

Temiakov D, Anikin M, McAllister W T. 2002. Characterization of T7 RNA polymerase transcription complexes assembled on nucleic acid scaffolds. *J Biol Chem.* 277 (49):47035-43).

U.S. Pat. No. 5,514,545. 1996. Eberwine, J. "Methods for characterizing single cells based on RNA amplification for diagnostic and therapeutics."

Maniatis T., Fritsch, E. F., Sambrook, J., 1982. Molecular cloning: A laboratory manual (CSHL)

European Patent No. 0 368 906 B2 (Gingueras et al.; discussing isothermal, exponential amplification ("3SR"))

U.S. Pat. No. 5,399,491 (Kacian et al.; discussing isothermal, exponential amplification) T Kievits et al., J Virological Meth 35 (Issue 3), December 1991, pp 273-286; EP 273086 (discussing NASBA)

Krieg & Melton. 1984. Functional messenger RNAs are produced by SP6 in vitro transcription of cloned cDNAs, *Nucleic Acids Res* 12, 7057-707 (discussing use of SP6, T4, T7 promoter sequences)

Melton, D. A., et al. 1984. Efficient in vitro synthesis of biologically active RNA and RNA hybridization probes from plasmids containing a bacteriophage SP6 promoter, *Nucleic Acids Res.* 12, 7035-7056.

US patent Application US2003/0082584 A1: "Enzymatic ligation-based identification of transcript expression", Shi L., et al.

U.S. Pat. No. 5,686,243

Syvanen A C. 2005 Toward genome-wide SNP genotyping. Nat Genet. 2005 June; 37 Suppl:S5-10.

U.S. Pat. No. 5,759,820 (Dynal AS) Homes E., et al. "Process for Producing cDNA"

Schouten J P, McElgunn C J, Waaijer R, Zwijnenburg D, Diepvens F. Pals G. 2002. Relative quantification of 40 nucleic acid sequences by multiplex ligation-dependent probe amplification. Nucleic Acids Res. 2002 Jun. 15; 30(12):e57.

Guatelli et al, "Isothermal, in vitro amplification of nucleic acids by a multienzyme reaction modeled after retroviral amplification", *Proc. Nat'l Acad. Sci. USA* 87, 1874-1878 (1990)

Kwoh et al, "Transcription-based amplification system and detection of amplified human immunodeficiency virus type 1 with a bead-based sandwich hybridization format", *Proc. Nat'l Acad. Sci. USA* 86, 1173-1177 (February 1989) (discussing transcription-mediated amplification using thermal cycling)

U.S. Pat. Nos. 5,716,785; 5,891,636, and 5,545,522 (Van Gelder et al.); Van Gelder et al, 1990 "Amplified RNA synthesized from limited quantities of heterogeneous cDNA", PNAS 87, 1663-1667S);

U.S. Patent Application (BioArray Solutions): "Multianalyte Molecular Analysis Using Application-Specific Random Particle Arrays" filed on Aug. 23, 2002, Ser. No. 10/204,799 (discussing Random Encoded Array Detection, READ™);

U.S. Patent Application (BioArray Solutions, hereinafter sometimes referred to as "eMAP"): "Multiplexed Analysis of Polymorphic Loci by Concurrent Interrogation and Enzyme-Mediated Detection" filed Oct. 15, 2002; Ser. No. 10/271,602;

U.S. Patent Application (BioArray Solutions, hereinafter sometimes referred to as "Multiplexed Expression Profiling"): "Optimization of Gene Expression Analysis using Immobilized Capture Probes," filed Oct. 26, 2004, Ser. No. 10/974,036, (including discussion therein relating to subtractive differential gene expression analysis; in the disclosure in the present application, sense and anti-sense strands are produced by incorporation of RNA pol promoter sequences);

U.S. Patent Application (BioArray Solutions): "Multianalyte Molecular Analysis Using Application Specific Random Particle Arrays" filed on Dec. 28, 2001; Ser. No. 10/032,657 ("Libraries of Encoded Magnetic Particles")

U.S. Patent Application (BioArray Solutions): "Nucleic Acid Amplification with Integrated Multiplex Detection" filed on Sep. 2, 2005; Ser. No. 11/218,838; see also Provisional Applications referenced therein: "Transcription Amplification System with Integrated Multiplex Detection; Functional Integration of Capture, Amplification and Multiplex Detection" filed Sep. 2, 2004; Ser. No. 60/606,666; "IVT-RT eMAP Assays; and Synthesis, Packaging and Screening of Random Encoded cDNA Libraries using IVT" filed Sep. 2, 2004; Ser. No. 60/606,666

U.S. Patent Application (BioArray Solutions): "Multianalyte Molecular Analysis Using Application-Specific Random Particle Arrays" filed on Aug. 23, 2002; Ser. No. 10/204,799 (discussing Random Encoded Array Detection, READ™);

U.S. Patent Application (BioArray Solutions): "Multianalyte Molecular Analysis Using Application Specific Random Particle Arrays" filed on Dec. 28, 2001; Ser. No. 10/032,657

U.S. Patent Application (BioArray Solutions): "Arrays of Microparticles and Methods of Preparation Thereof," filed on Jul. 9, 2002; Ser. No. 10/192,352

U.S. Patent Application (BioArray Solutions hereinafter sometimes referred to as "PARSET™"): "System and Method for Programmable Illumination Pattern Generation," filed Jan. 24, 2001, Ser. No. 09/768,414

U.S. Pat. No. 6,251,691 (BioArray Solutions, hereinafter sometimes referred to as "LEAPS"): "Light Controlled Electrokinetic Assembly of Particles Near Surfaces": see especially FIG. 8;

U.S. Pat. No. 6,291,170

U.S. Pat. No. 5,686,243

US Patent Applications 2005/0130194 and 2005/0123943
U.S. Pat. Nos. 5,283,174, 5,639,599 Arnold
U.S. Pat. No. 6,291,170
U.S. Pat. No. 6,004,745
U.S. Pat. No. 4,683,202
U.S. Pat. No. 6,797,524 BAS
U.S. patent application Ser. No. 10/973,700
U.S. patent application Ser. No. 10/348,123
U.S. Provisional Patent Application 60/628,464

SUMMARY OF THE INVENTION

Disclosed are the single-stranded primer-promoter-selector construct and the methods mediated by in-vitro transcription, using a aforementioned single-stranded primer-promoter-selector construct (a format also referred to herein for convenience as single-stranded template IVT (sst-IVT)) message abundance and allele copy number determination for: multiplexed gene expression analysis; multiplexed allele counting; analysis of gene copy number polymorphisms; and allele discrimination for the identification of mutations and polymorphisms. The single-stranded primer-promoter-selector construct consists of three functional independent parts linked in a way to orient IVT for amplification of selector sequence only, in the direction opposite to any possible primer 3' extentions.

Generally, all methods of the target amplification begin with target—specific annealing of primer part of the contract followed by elongation, reverse transcription, or ligation of the primer to another oligonucleotide. The construct generally comprises a sequence-specific target priming subsequence, a T7 (or T3 or SP6 other suitable) promoter subsequence (template strand) and a selector subsequence that is tentatively uniquely associated with a particular priming subsequence. In the sst-IVT reaction, the T7 (or other) promoter sequence is oriented to direct the transcription in the direction opposite to that of reverse transcription (RT) (or more generally elongation, in the case of a DNA template; see FIG. 1). As a result, sst-IVT as disclosed herein and in contrast to conventional formats of IVT, amplifies a sequence that is not part and designed not to be any part of the original target. The RNA template for sst-IVT can be a messenger RNA (mRNA) or viral genomic RNA, or more generally, an RNA product produced by a previous IVT reaction. The methods of the invention are also useful for the analysis of gDNA, for example following denaturation (to produce single-stranded target) and/or fragmentation (Maniatis T., 1982). The performance and efficiency of the sst-IVT reaction can be improved using a selector as single stranded DNA template but with a double-stranded (ds) T7 promoter subsequence (one such strand incorporated in the primer (template); the other annealed thereto (non-template).

To produce a template for sst-IVT, an elongation or reverse transcription (RT) reaction can be performed to extend the primer after annealing to target strands of interest. To facilitate the subsequent separation of the extension product from unused primer, this reaction can be performed with modified dNTPs, e.g., dNTPs modified with biotin or other haptens, so that, following completion of, for example, the RT reaction, cDNA products containing the modified dNTPs can be captured to a solid phase. The separation step also can be performed using column purification, obviating the need for modified dNTPs.

In one embodiment, sst-IVT can utilize an RNA-DNA heteroduplex as a template wherein the cDNA produced by reverse transcription using the primer-promoter-selector construct remains annealed to the intact original mRNA. In one variant, the sst-IVT reaction can be performed with the RNA-DNA heteroduplex attached to a solid phase matrix.

The sst-IVT reaction produces a number of RNA fragments equal in length and complementary in sequence to the selector subsequence. Preferably, this selector subsequence (and its complementary sequence) is designed to be dissimilar to any other sequence present, or expected to be present, in the reaction. It can serve as a unique capture sequence for subsequent solid phase reactions, preferably performed on encoded microparticles ("beads") in a Random Encoded Array Detection (READ™) format (see U.S. Pat. No. 6,797,524). Capture to probes displayed on encoded solid-phase carriers permits optical detection of RNA products labeled by incorporation of modified NTPs or detection of elongation products formed by template-mediated, reverse transcription catalyzed probe elongation ("eMAP" see U.S. application Ser. Nos. 10/271,602; and 11/218,838) using modified dNTPs; FIG. 1.

The protocols disclosed herein (and as depicted in FIGS. 2, 3, and 4) enable the substantial simplification, and acceleration of complex applications, as described further below. These protocols have the following advantages (where statements made for RNA targets and RT apply, mutatis mutandum, to DNA and primer extension):

only a single functional primer is used, and second DNA strand synthesis, in practice requiring in one embodiment the digestion of the mRNA template and the introduction of a second primer and a DNA polymerase, is not necessary and can be eliminated;

the RNA digestion step with RNaseH, normally required to permit second strand synthesis, also may be eliminated; the presence of mRNA-cDNA heteroduplex does not interfere with sst-IVT because the reaction uses only the T7 and selector sequences which are not part of the heteroduplex;

the target-specific primer may be placed anywhere along the mRNA target of interest, without affecting the transcript sequence or length, which are determined by sequence and length of the selector sequence; transcripts are short in order to maximize the efficiency of transcript capture to encoded microparticles (see application Ser. No. 10/974,036), as described below; transcripts have dissimilar sequences, thereby allowing detection and counting of different genes, as well as of genes within gene families displaying significant sequence similarity;

the comparative simplicity of the protocol permits the combination of several steps, as described herein in greater detail, including concurrent target capture, amplification, and multiplexed detection in "single-tube" and homogeneous formats, preferably using the READ format. Integration in turn facilitates miniaturization, as described herein.

BRIEF DESCRIPTION OF THE FIGURES

FIG. 2 depicts a method for multiplexed gene expression analysis using the constructs and methods described herein.

FIG. 3 depicts elongation-mediated detection of SNPs or mutations using the constructs and methods described herein.

FIG. 4 depicts ligation-mediated detection of SNPs or mutations using the constructs and methods described herein.

FIG. 5 demonstrates that, based on signal generated following detection, the sst-IVT reaction is dependent on the sequence and concentration of the constructs described herein.

FIG. 9 shows devices and methods for magnetic capture—flow-through purification, and membrane purification of the assay product from construct excess.

FIG. 10 shows the relative signal generated at both 100 milliseconds and 500 milliseconds of exposure, following the IVT reaction with different templates-constructs described in figure legend (with and without an NT portion for the T7 promoter added and with and without digestion of mRNA by RNaseH).

FIG. 14 shows some closely homologous maize sequences with polymorphic sites shown in bold.

DETAILED DESCRIPTION

As noted above, the primer-promoter-selector constructs for use in the methods disclosed herein comprise up to three different subsequences, each of designated length, namely: the gene-specific primer sequence, the template strand sequence for T7 (or other) promoter, designed to direct in-vitro transcription toward the 5' end of the construct; and a unique "selection" or "selector" sequence. The method of the invention directs IVT to proceed so as to produce RNA copies of the selector sequence. The RNA transcripts are detected by capture to encoded microparticles ("beads") displaying probes matching specific selector sequences. Unique selector sequences render the products of the reaction unique and permits selection of specific amplicons from a set of targets of (originally) similar sequence (see also Section 2.2, Allele Counting). All messages are "counted", regardless of whether the RT reaction in which they serve as templates produces cDNA product of full or only partial length, the latter reflecting aborted RT reactions. Preferably, for detection of specific messages within a background of similar messages, as well as for detection of mutations or polymorphisms, pairs of allele-specific constructs are used so that only a matching primer sequence in the construct mediates elongation and formation of amplified transcripts. This approach is particularly useful for the detection and analysis of a designated subset of mRNAs, viral genomic RNA/DNA, alleles, and genes.

1. In-vitro Transcription Using Primer-Promoter-Selector Constructs-general Properties Example I illustrates the performance of sst-IVT under relevant reaction conditions, using a construct comprising sequence-specific RT primer, T7 promoter and a selector subsequence that is uniquely associated with the RT primer. As shown, the sst-IVT reaction displays a sequence-specific dose response, with a limit of detection—in the model system—of ~1 fmol of primer/rxn (here, as elsewhere, unless stated otherwise, the volume of the reaction ("rxn") is 10 ul). Addition of non-template strand increases the signal intensity ~10-fold over a significant range of target concentration, but has no effect on the limit of detection (FIG. 5). Thus, the signal intensities attained in the assay permit sst-IVT to be performed either with, or without, addition of the non-template strand of the T7 promoter, depending on the requirements of specific applications.

Figure 6:
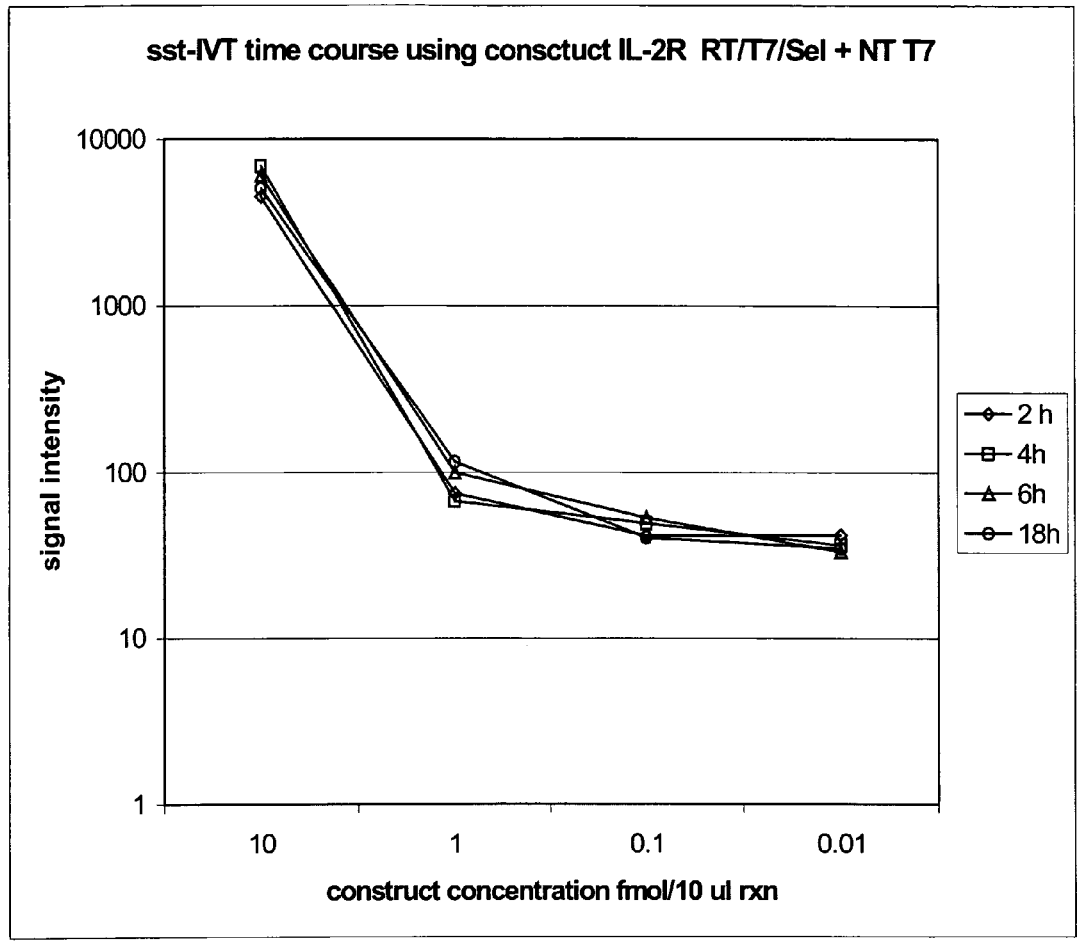
FIG. 6 shows the time course for sst-IVT reaction for different starting concentrations of the construct IL-2R RT/T7/Sel and NT portion for T7 promoter.

The time course of the sst-IVT reaction, illustrated for IL-2R RT/T7/Sel ssDNA+NT T7 producing short RNAs, is shown in FIG. 6. The reaction is very fast initially, and largely complete within $\leq$2 hours, though a further improvement in yield is observed for low concentrations of the template (1 fmol/rxn) after 4 h of incubation.

2. RNA Analysis 2.1 mRNA Counting: Determination of Message Abundance

The method of the invention permits the realization of a format for rapid gene expression profiling; that is, the simultaneous determination of the respective abundances of a set of designated messages (typically in the presence of other messages). This will be of particular interest for applications involving the monitoring or profiling of patterns of expression of a set of specific genes in response to external stimuli such as therapeutic or infectious agents.

The current protocol includes 4 steps (FIG. 2):
1. cDNA synthesis (by reverse transcription) using RT primer/T7/selector constructs
2. Removal of unused constructs—in one mode, by capture of cDNA
3. Linear amplification of selector sequences corresponding to individual cDNAs
4. On-chip detection of RNA products by reverse transcription/hybridization Alternatively, steps 3 and 4 can be combined:
3. Simultaneous amplification/detection using a "co-assembled" array of microparticles, as described in greater detail below.

Figure 7:
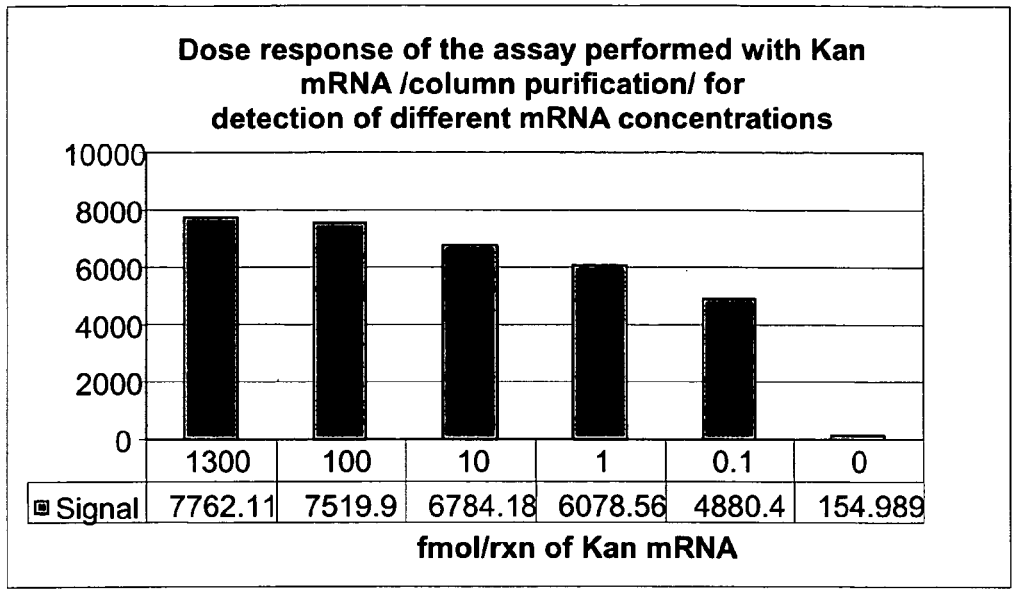
FIG. 7 shows the dose response of an assay, using the constructs as described herein, for detection of different mRNA concentrations (kanamycin mRNA).

Example II demonstrates sensitivity of the assay using model Kanamycin mRNA over a range of target concentration from 1300 fmol/rxn to 0.1 fmol/rxn. This variant of the assay employs column purification (not magnetic separation) and thus will not require biotinylated (or otherwise modified) dNTPs for cDNA synthesis. The assay, in this format, demonstrates a dose response with a detection limit of 0.1 fmol/rxn (FIG. 7).

Removal of Unused Primer ("Clean-up")—Unused primer-promoter-selector construct must be carefully removed prior to initiating sst-IVT to prevent the formation of transcripts from unused primers alone. That is, depending on the amount of carry-over, sst-IVT can produce a target-independent signal whose intensity can limit the sensitivity of the assay.

Moreover, usage of biotinylated (or other hapten-ated) dNTPs for cDNA synthesis requires removal of unused nucleotides prior to capture on streptavidin (or hapten-AB) coated magnetic or non-magnetic particles.

The removal of dNTPs is also desirable in order to improve the degree of incorporation of fluorescently labeled dNTPs during a downstream on-chip RT-eMAP reaction (which otherwise tend to be excluded in favor of unlabeled dNTPs) and thus to enhance the assay signal intensity.

Several methods of purification are provided herein. In one standard approach, an exonuclease treatment, to digest excess RT primer, is combined with an alkaline phosphatase treatment, to remove dNTPs prior to the IVT reaction (using, for example ExoSap-IT,#78200,USB).

In another approach, excess primers and NTPs can be removed from the reaction by column purification (see also Example II). To ensure effective separation of primers from cDNA or elongation product, primers should be substantially shorter than products.

In the third approach the column purification can be combined with ExoI construct digestion. The efficiency of removing unused primer using a combination of Exonuclease I treatment and column purification is shown in Example III. The results suggest that the optimal primer concentration in the current versions of the assay protocols should not exceed 100 fmol/rxn. ExoI treatment improves the signal/noise ratio (by further reducing the residual concentration of RT primer) but does not increase the permissible primer concentration.

Another method of removing excess construct is by capture to magnetic beads, and separation of the beads by magnetic attraction. This method has the additional advantage of facilitating the integration of IVT and elongation in an "on-chip" format.

Magnetic separation can be performed in at least three (3) different flow-through configurations, as shown in FIG. 9, namely using a "tip on magnet," a nanosep device (Pall, see Catalogue) or a nanoreactor (as depicted in FIG. 9). The sst-IVT protocols invoking magnetic separation use a mixture of biotinylated and unmodified dNTP's for cDNA synthesis, followed by capture of the biotinylated product using Streptavidin-coated magnetic nanoparticles. Another (fourth) configuration for clean-up of magnetic beads is to collect the beads by centrifugation from 1 ml of wash buffer in regular 1.5 ml tubes, then place the tubes next to a magnet to lift the pellet up along the tube wall, then remove all the wash buffer form the bottom of the tube; and repeat this procedure 2-3 times up to complete primer removal.

Attachment of cDNA to a solid phase matrix, including beads and microparticles, right after cDNA synthesis in the current protocol, permits separation, purification, and significant concentration of the cDNA in a small volume, and thus has potential to increase assay sensitivity.

The particles can be of any suitable type (see, e.g., U.S. application Ser. Nos. 10/973,700; 10/348,123, both incorporated by reference) including magnetic capture particles (see, e.g., U.S. application Ser. No. 10/032,657, incorporated by reference) which allow the elongation product, bound to the particle, to be concentrated near or on a substrate surface by application of a magnetic field.

The assay format of the present invention offers the following advantages as described below:

Design Flexibility—by permitting the placement of the priming sequences anywhere along the mRNA, the sst-IVT reaction disclosed herein elimates the requirement for primer placement close to the 5' end of the mRNA of interest—in order to limit the size of the product to be detected by on-chip detection as described in U.S. application Ser. No. 10/974,036—or close to the 3' end, as required by conventional gene expression methods, thus improving the flexibility of design. In addition, by producing transcripts differing in sequences regardless of the degree of similarity in the original target sequences, the specificity of multiplexed analysis is substantially enhanced.

Short Transcripts of Specific Sequence—the target-specific primer may be placed anywhere along the mRNA target of interest, without affecting the transcript sequence or length which are determined by sequence and length of the selector sequence; in order to maximize the efficiency of transcript capture to encoded microparticles (see U.S. application Ser. No. 10/974,036), as described below, transcripts are preferably short.

The specific and unique sequence of sst-IVT selector sequences in the constructs, and use of primer designs and ligation of constructs (as described herein) allows introduction of significant sequence dissimilarity among homologous messages to allow distinguishing between expression of similar genes. This is a design feature that is especially beneficial for analysis of specific genes within gene families; for example, gene copy counting; and distinguishing a set of cytokine messages or Maize gene families messages.

Elimination of Second Strand Synthesis—A cumbersome aspect of current protocols for gene expression analysis is the need for second strand DNA synthesis, which in turn requires digestion (or removal) of the RNA template. While the DNA polymerase activity of certain reverse transcriptases can catalyze DNA synthesis, in practice, a DNA polymerase must be added to the reaction following mRNA digestion. One widely used protocol (U.S. Pat. Nos. 5,545,522; 5,514,545; Gubler, V., 1983) relies on random priming, but requires addition of a ligase, bringing the requisite number of enzymes to three (prior to addition of the RNA polymerase for IVT). However, particularly if the designated set of messages of interest is given, the methods of the present invention permit substantial protocol simplification.

Binding of the RNA polymerase and its progression toward the 5'end of the construct occur with substantial efficiency even in the absence of a double-stranded promoter sequence. That is, following first strand (cDNA) synthesis and removal of unused primer—preferably via capture of the cDNA to a solid phase, or by column purification—the IVT reaction produces copies of the selector sequence. Preferably, the non-template (NT) T7 strand can be added as part of the IVT buffer to enhance the amplification gain by a factor of ~10, possibly reflecting an increase in binding affinity of the RNA polymerase when encountering the double-stranded promoter sequence.

Figure 11:
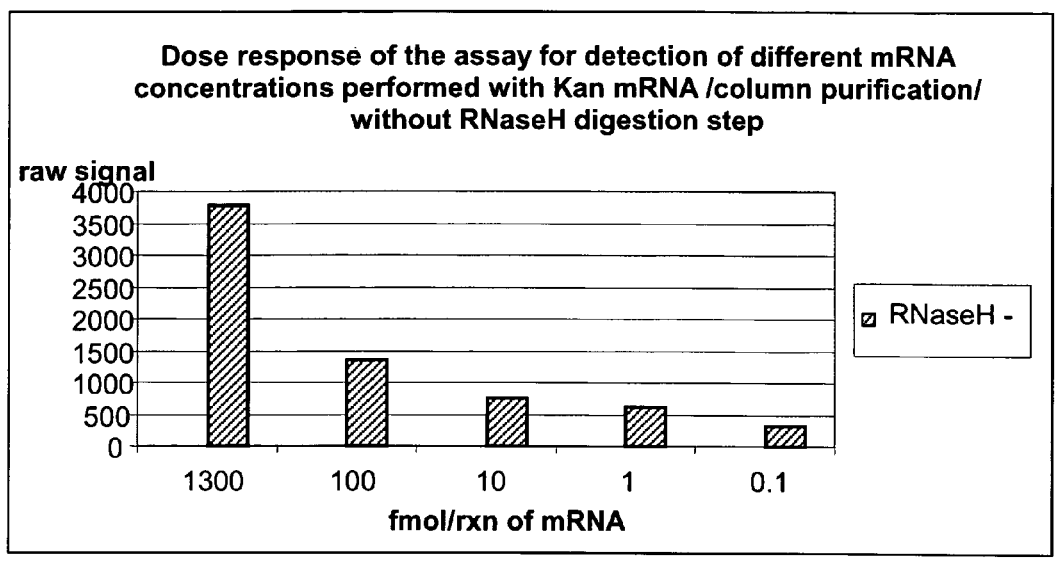
FIG. 11 shows an assay performed using the constructs described herein for detection and amplification of Kanamycin mRNA, including column purification and eliminating the RNaseH digestion step of mRNA.

Elimination of RNaseHDigestion—In the current protocol for gene expression analysis, the template for sst-IVT forms part of the RT primer construct and remains in single stranded form after cDNA synthesis. Example IV demonstrates experiment performed to determine if the conventional step for RNaseH digestion of RNA—otherwise required in a conventional double-stranded IVT reaction to permit second strand cDNA synthesis—might be omitted. Using a model construct for the sst-IVT reaction (FIG. 10) and the whole assay protocol (FIG. 11), the experiments described in Example IV demonstrate that the presence of the RNA/DNA heteroduplex adjacent to the T7 promoter does not interfere with annealing of the NT strand to the template promoter strand and has no effect on RNA synthesis, suggesting that RNaseH digestion can be eliminated from the protocol, and providing a substantial additional assay simplification.

Solid Phase IVT—Solid phase IVT permits the implementation of magnetic "clean-up" steps, as described herein, following reverse transcription (or more generally primer elongation) to remove unused primer. Further, magnetic capture using, for example, magnetic traps of suitable design (see, e.g., three types of micromachined inductors, namely, spiral type, Ahn et al, J. Micromech. Microeng. 3, 1-9, (1993), solenoid type, Ahn et al, IEEE Transactions Comp., Packag. Manufact. Technol. 17, 463-469 (1994) and toroidal meander type, Ahn et al, IEEE Trans. Indus. Elec 45, 866-875 (1998) (all incorporated by reference) permit the confinement of transcripts to a solution of minimal volume. Prior to capture of biotinylated cDNA (and with it, the annealed RNA target) to Streptavidin-coated magnetic particles, unincorporated biotinylated dNTPs preferably are removed (for example by alkaline phosphatase treatment or by column purification) in order to enhance the capture efficiency which is otherwise impaired by the competition from biotinylated dNTPs.

Figure 12:
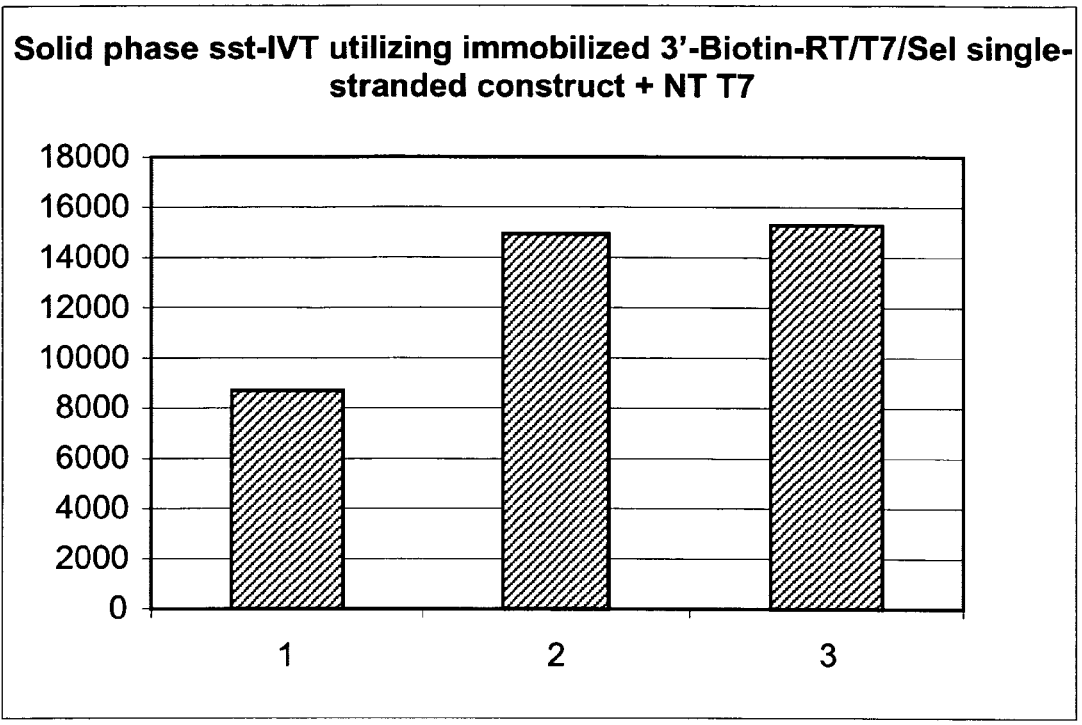
FIG. 12 shows results for solid-phase sst-IVT with primer-T7-selector constructs immobilized to streptavidin coated microbeads followed by RT eMAP detection.

Example V provides a comparison of the efficiency of sst-IVT reactions performed in solution and performed on the solid phase, using a biotinylated ssDNA RT primer model compound. It is seen that solid phase sst-IVT, under the conditions selected, has a yield of approximately half that of the reaction in solution (FIG. 12). However, the signal intensity produced by the solid phase reaction, obtained at a concentration of 10 fmol/ul of the model compound, shows that the reaction is sufficiently efficient to be used as part of an integrated assay protocol.

Figure 13:
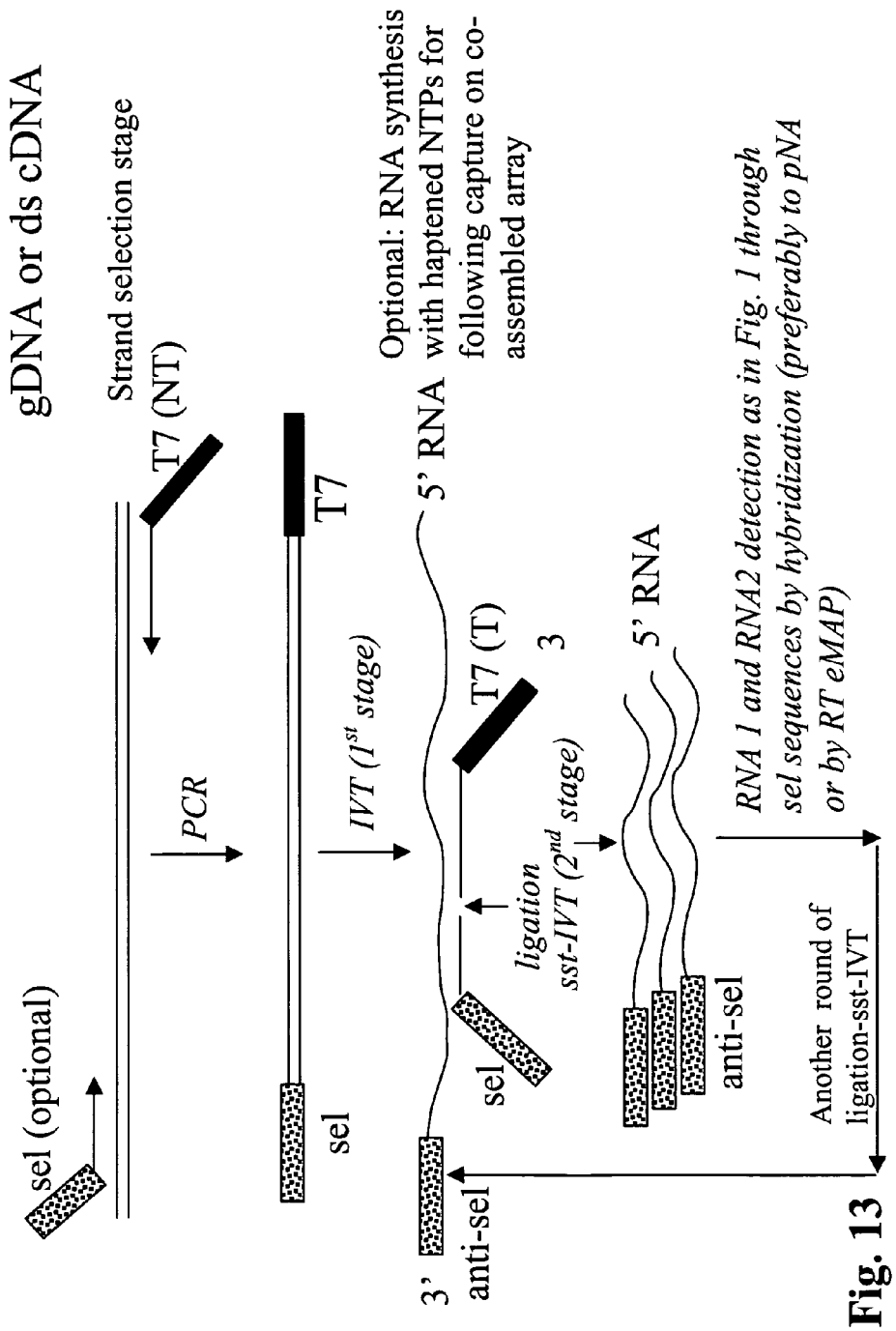
FIG. 13 depicts multiple rounds for high-yield IVT (coupled ligation—sst-IVT reactions) amplification method using the constructs described herein.

Two-stage IVT Amplification—Another aspect of the invention is the application of sst-IVT in multiple rounds of amplification with intervening ligation steps, thus skipping the conventional cDNA synthesis (see U.S. Pat. No. 5,514, 545) (FIG. 13). This method can be applied to mRNA detection with prior cDNA and second strand synthesis, as well as to genomic DNA analysis. Initially, in this method, PCR is used to amplify the sequence of interest with introduction of T7 promoter region at one end and, optional, sel sequence at the other end of the PCR product.

After that, the RNA is produced by a conventional IVT reaction with the gain in the range of $10^2$ to $10^3$, whereas conventional IVT can be used as a method of amplicon strand selection with respect to which particular primer contains T7 promoter sequence (as described in the copending application Ser. No. 11/218,838). The resultant RNA can be used next as a template for annealing of promoter oligonucleotides and selector oligonucleotides (as shown in FIG. 4, first version) followed by ligation. The resultant promoter-selector construct, amplified by means of sst-IVT, produces an additional gain in the range of $10^2$ to $10^3$. Thus the original RNA can be amplified by $10^5$-$10^6$, and detected by means of a corresponding selector sequence.

Differential "sample-control" expression profile analysis.
The standard methods for expression analysis always rely on comparison of sample of interest "case or diseased/altered tissue/cell" with a reference "control or normal" sample, or on differences in expression in transgenic vs. normal plants. This invention also covers the relative gene expression determination using the advantages of sst-IVT. The conventional methods for relative gene expression analysis rely on determination of ratio intensities of different signals, obtained following the assay step, for both the "case" and "control" samples (U.S. Pat. No. 6,110,426).

Figure 1:
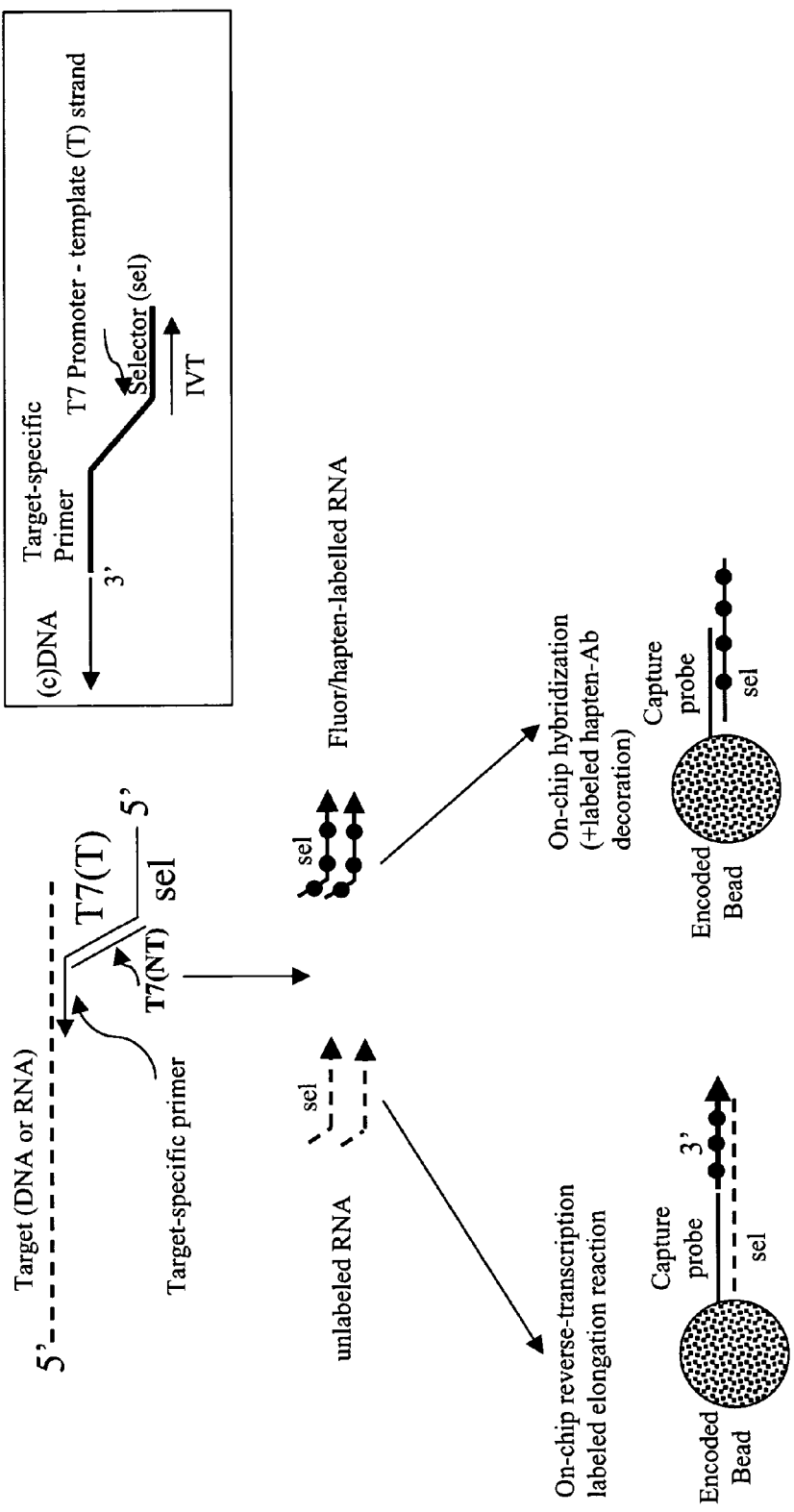
FIG. 1 depicts, for the primer-promoter-selector constructs described herein, the directions of RT (or primer elongation) and in vitro transcription, as well as detection of products generated with either hybridization-mediated detection or elongation-mediated detection.

The same strategy can be applied to relative gene expression monitoring. Differential two color staining can be achieved by incorporation of different fluorescent NTPs into "case" RNA and "control" RNA products during separate sst-IVT reactions, followed by two colors detection of the products by hybridization capture (FIG. 1). Alternatively, different "selector" sequences can be designed for "case" and "control" RNA products for separate sst-IVT reactions using single color detection.

Another possibility to determine the relative gene expression profile is to use single color subtractive detection method (U.S. Patent No. WO2005042763, BAS). To this end the selector sequences for "case" and "control" have to be designed as reverse complement and capable of forming a double stranded duplex. At the assay stage of detection of RNA products (namely RNA and aRNA), two separate reactions for case and normal samples are mixed together under conditions permitting the formation of RNA-RNA duplexes. The excess of RNA or aRNA product can be captured to appropriate sense and anti-sense capture probe on beads in a co-assembled single array, and detection of the product can be performed either by RT eMAP or by hybridization, as in FIG. 1, thus showing under- or over-expression of particular gene or set of genes in "case" sample.

2.2 Allele Counting

Allele-specific reverse transcription or allele-specific ligation can be combined with sst-IVT for multiplexed allele counting, for example, to selectively determine the expression pattern of designated genes in the presence of similar genes and for the detection of allele polymorphisms (Syvanen A. C., 2005).

2.2.1 Reverse Transcription-mediated Analysis

Allele-specific reverse transcription is combined with IVT in an assay protocol comprising the following four steps (FIG. 3):

1. Annealing of allele-specific reverse transcription primer, with T7/selector and cDNA synthesis by reverse transcription; (in case of DNA analysis: primer extension using DNA polymerase);
2. Removal of unused primer (using one of the available methods described herein);
3. Transcription of the selector sequence; and
4. On-chip detection of resulting RNA by reverse transcription or hybridization.

The principles of the method resembles those illustrated in Example II, except that now, the 3' end of the target-specific primer is designed for specific alleles such that primer extension occurs only if primer and target are matched at (and near) the 3' end of the primer sequence. In a preferred embodiment, a pair of primers differing in composition at the 3' end may be used to discriminate between two alleles.

2.2.2 Ligation-mediated Analysis

Allele-specific ligation using an RNA template (U.S. Pat. No. 5,686,243, US Patent Application No. US 2003/0082584 A1) is combined with IVT to ensure allele-specific linear amplification in a protocol comprising the following four steps (FIG. 4):

1. Annealing of two oligonucleotide probes—one the "promoter", the other the "selector"—to the mRNA template, immediately adjacent to the designated variable site of interest;
2. Ligation of the probes to produce an intact promoter-selector construct;
3. Transcription of the selector sequence;
4. On-chip detection of resulting RNA by reverse transcription or hybridization.

"Promoter" and "Selector" Oligonucleotides—For each target of interest, the two oligonucleotides are designed to match the template on either side of the site of interest. Ligation (by T4 DNA ligase, or Taq DNA ligase, New England Biolabs) of the promoter and selector oligonucleotides produces an intact promoter-selector construct. The intact construct is produced only if either the promoter oligonucleotide sequence, at its 5'end, or the selector oligonucleotide sequence, at its 3'end, matches the target sequence at the site of interest. Promoter-selector construct serves as a template for the sst-IVT reaction, which produces RNA copies of selector, which is then detected. That is, target alleles other than the allele of interest, will not mediate the formation of an intact IVT promoter-selector construct and thus will not be counted. Thus, the method permits the counting of specific mRNA sequences in the presence of other mRNA sequences that differ from those of interest by as little as a single nucleotide, as in the case of the certain gene families in Maize hybrids demonstrated in Example VI (See FIG. 14) and more generally in the case of other gene families. Conversely, if all alleles are to be counted, multiple degenerate primer oligonucleotides can be provided to match normal or variant alleles at the designated site.

Generally, in this format, the RNA template should be removed or digested (by standard methods) prior to initiating sst-IVT. As with mRNA counting, the efficiency of the reaction is improved by addition of the non-template strand of the promoter (preferably as part of the IVT reaction buffer). A major advantage of this method is that it eliminates the need for a purification step: unused primer will not be connected to the selector subsequence and thus will not be detected.

Another alternative is to use ligation instead of reverse transcription to introduce a capture moiety such as biotin into a sst-IVT template strand by linking a primer-promoter-selector construct with a second "capture" oligonucleotide containing the capture moiety at its 3' end (as shown on FIG. 4; second version). As with mRNA counting, this format will require removal of unused primer.

The resultant biotinylated construct can be used for the purpose of concentration after ligation in small volume or for placement of the construct into a co-assembled array along with detection beads.

3. DNA Analysis

The methods of the invention are readily adapted to the analysis of gDNA or amplicons produced by PCR. In the preferred embodiment, a primer-promoter-selector construct is directed against a DNA subsequence of interest. Then, under conditions (e.g. denaturation of ds DNA target by heating) permitting annealing of the construct to single-stranded DNA, the construct is extended in a DNA polymerase catalyzed reaction when matched at or near the 3'end (FIG. 3).

Figure 15:
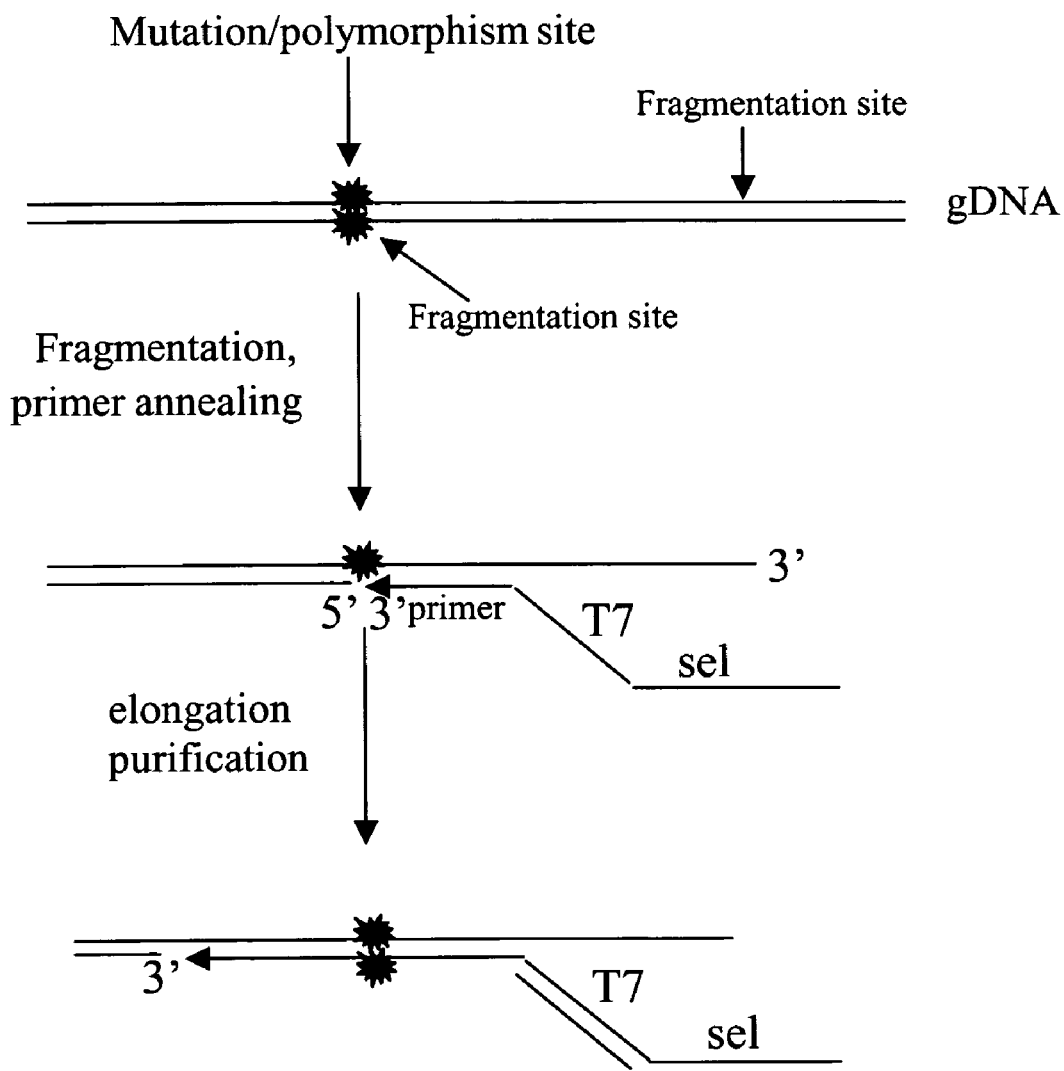
FIG. 15 Fragmentation of gDNA with following extension of introduced primer.

As an alternative, to introduce the T7 sequence into gDNA (or DNA amplicons), the double-stranded target is first degraded chemically (Maniatis T., 1982) leaving cohesive 3' ends for possible annealing of the target-specific construct. Then, by means of strand displacing versions of a DNA polymerase, the primer is extended, thus introducing the T7 sequence (FIG. 15). Following removal of unused target-specific primer, the elongated product is used for sst-IVT amplification of the selector subsequence, followed by detection as shown in FIG. 3.

3.1 Analysis of Gene Copy Number Polymorphism

The presence of multiple copies of chromosomes and genes is known to be associated with several disorders, for example: Down's syndrome (Dutta S., 2005) and Spinal muscular atrophy (SMA) (Ogino S., 2004) as well as with several types of cancer: breast cancer (Seo, M. Y., et al., 2004), skin cancer (Sellers, W. R. 2005) and others. Gene copy number may predict patient response to treatment with a particular drug, e.g., lung cancer treatment with gefitinib (Hirsch F. R. 2005). Rapid and convenient formats of analysis are thus desirable for routine clinical applications.

When only a single gene or small number of alleles is of interest, as is frequently the case in practice, the methods of the invention preferably are used in combination with detection of RNA product in solution. To this end, a variety of standard methods are available, including the use of the hybridization protection format (see, e.g., Arnold et al. in U.S. Pat. Nos. 5,283,174 and 5,639,599) or the use of a fluorescence energy transfer format using molecular beacons (Vet et al., 2002) or probes in "looped" configurations whose transformation upon transcript annealing produces a change in fluorescence (see U.S. patent application Ser. No. 11/218, 838; filed Sep. 2, 2005).

In a preferred embodiment, aliquots containing increasing amounts of a reference sample (with known copy number) are added to a preset amount of the clinical sample of interest, and the intercept of the resulting plot of intensity versus amount of reference sample with the intensity axis indicates the gene copy number in the clinical sample.

The sensitivity of detection is increased when molecular beacons or "looped" probes (see also U.S. application Serial No. filed Nov. 16, 2004; Ser. No. 60/628,464 relating to "looped probes") are displayed on solid phase carriers such as microparticles; magnetic microparticles may provide additional advantages. When combined with these methods of detection, the methods of the invention also permit real-time monitoring of the amplification reaction.

3.2 Allele Discrimination

Variable sites in a DNA sequence representing mutations or polymorphisms can be analyzed using the methods of allele-specific analysis described herein, using allele-specific primers for DNA polymerase catalyzed extension. Similarly, the methods of ligation-mediated analysis described above for RNA analysis is readily adapted to DNA analysis, using single-stranded DNA as the template for ligation. The major difference from conventional ligation-mediated alleles and SNPs discrimination (Schouten J P., 2002) is application of the IVT reaction instead of PCR to amplify constructs following ligation. As with the RNA analysis, the ligation-mediated method has the significant advantage of eliminating the need for the removal of oligonucleotide probes and primers, thus facilitating the realization of homogeneous assay formats. This will be especially desirable when applying the methods of the invention to pathogen screening, including the detection and identification of viral pathogens, especially when combined with the concentration of viral RNA with subsequent amplification and detection, as described in greater detail below.

4 Integration of Protocol Steps 4.1 IVT with Concurrent Detection of Products: Co-Assembled Bead Array Also described herein are methods for combining the linear amplification of gDNA, cDNA or RNA to generate RNA products and the concurrent detection of these products using a parallel format of detection, preferably Random Encoded Array Detection (READ™).

Short a-sel RNA transcripts produced by sst-IVT can be detected as they are being produced, for example by solid phase reverse transcription to elongate capture probes or by capture to molecular beacons (supra) or probes in "looped" configurations, whose transformation upon transcript annealing produces a change in fluorescence (Vet, J. A. M., 2002). To enhance the capture efficiency under the conditions of low ionic strength permitting efficient IVT, peptide nucleic acid (PNA) capture probes (see application Ser. No. 10/227,012) can be used to advantage.

As noted above, the integration of sst-IVT with subsequent multiplexed detection would eliminate additional steps in the assay protocol, thereby enhancing speed, reducing reagent consumption, and reducing the potential for sample contamination and error arising from sample handling. The combination of analysis and detection directly on-chip, preferably in an enclosed compartment, would be particularly desirable. To this end, this invention discloses formats of concurrent on-chip IVT amplification and detection of resulting RNA by means of reverse transcription.

Figure 16:
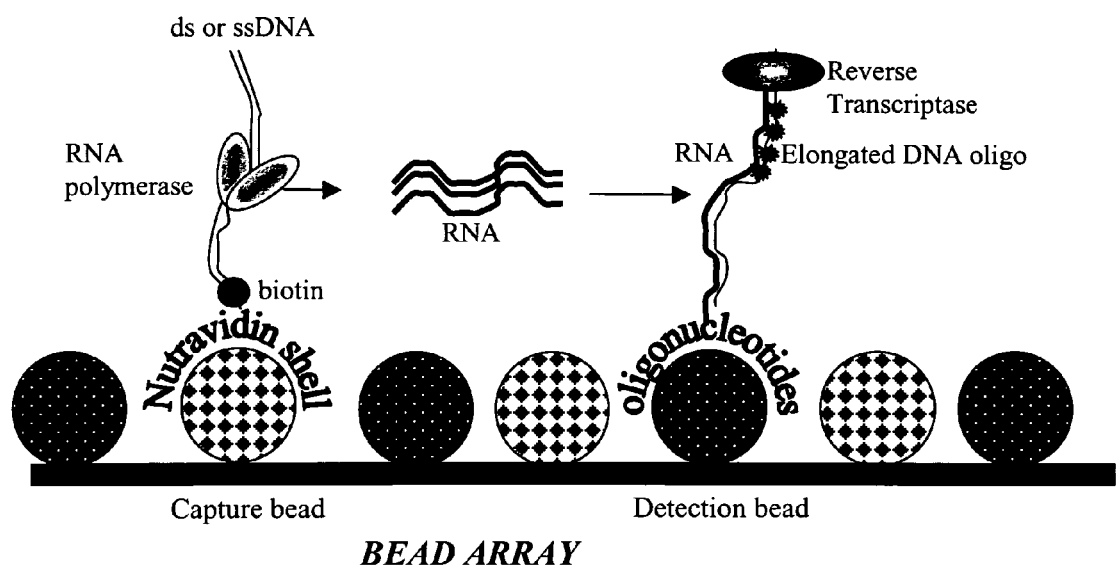
FIG. 16 shows a co-assembled bead array where the sst-IVT reaction using immobilized primer-T7-selector construct described herein or dsDNA is carried out in integrated fashion with detection of resulted RNA by capture-mediated elongation.

In one embodiment, a random array of encoded beads is co-assembled to contain beads displaying template capture probes as well as product analysis probes. As illustrated in FIG. 16, such a co-assembled array may include neutravidin-coated beads (or magnetic beads) to capture biotinylated cDNA (or beads displaying other capture moieties, for example antibodies, directed against corresponding haptens incorporated into the cDNA target strand), and encoded beads displaying oligonucleotide probes with selector sequences to permit detection of specific RNA strands produced in the sst-IVT reaction to permit detection (for example following elongation with labeled nucleotides).

Figure 17:
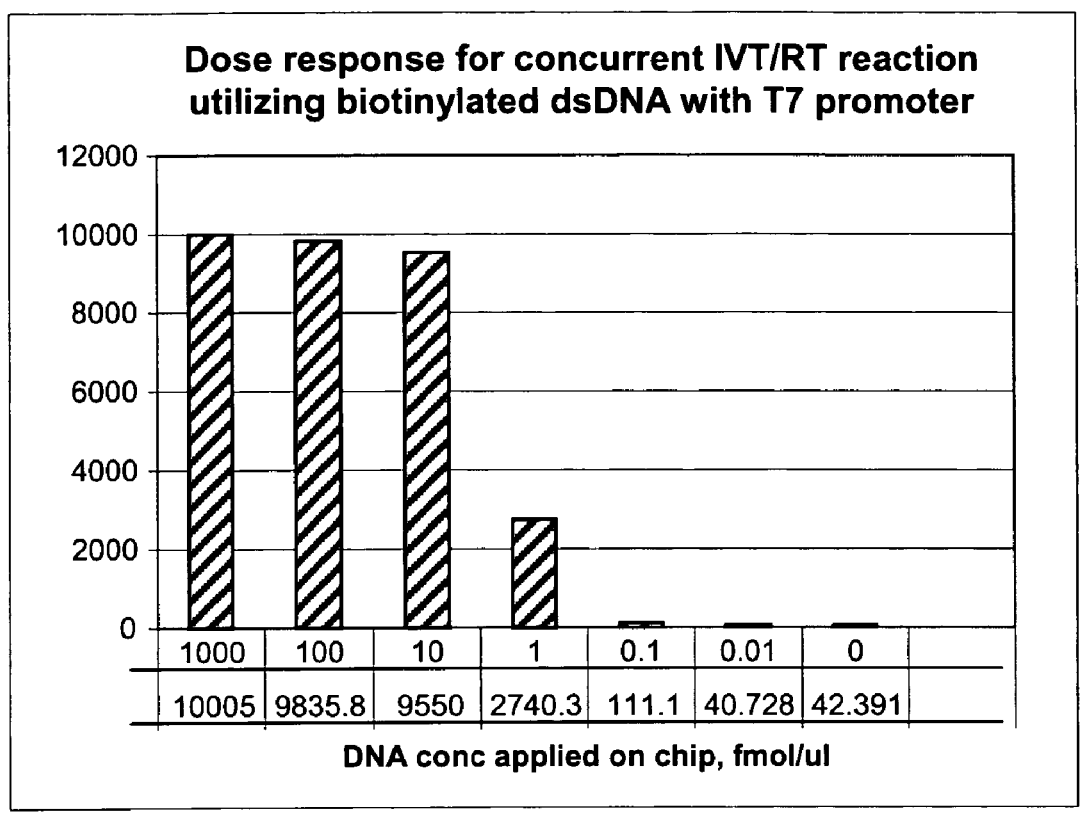
FIG. 17 shows results of concurrent IVT/RT reaction using different concentrations of biotinylated dsDNA immobilized on a co-assembled bead array.

One of the possible implementations for Concurrent Amplification and On-chip Detection is described in Example VII. As shown in FIG. 17, the concurrent reaction exhibits a dose response, with a limit of detection of 1 fmol/ul of a model biotinylated dsDNA applied to the chip. As we have demonstrated previously, the solid phase IVT can be performed using single-stranded templates as well. These results demonstrate the feasibility of combining sst-IVT with RT-mediated probe elongation for detection, in a format permitting the reaction to be miniaturized and configured in sealed compartments. This format of co-assembly permits sst-IVT with concurrent product analysis to be performed (following capture of the cDNA or other IVT or sst-IVT templates such as the ligated oligonucleotide probe pair) in a total reaction volume of less than 1 microliter, and more preferably of less than 50 nanoliter (using, for example, a configuration such as that shown in U.S. application Ser. No. 11/218,838, filed Sep. 2, 2005)

4.2 RNA Capture, Amplification and Multiplexed Detection

Figure 18:
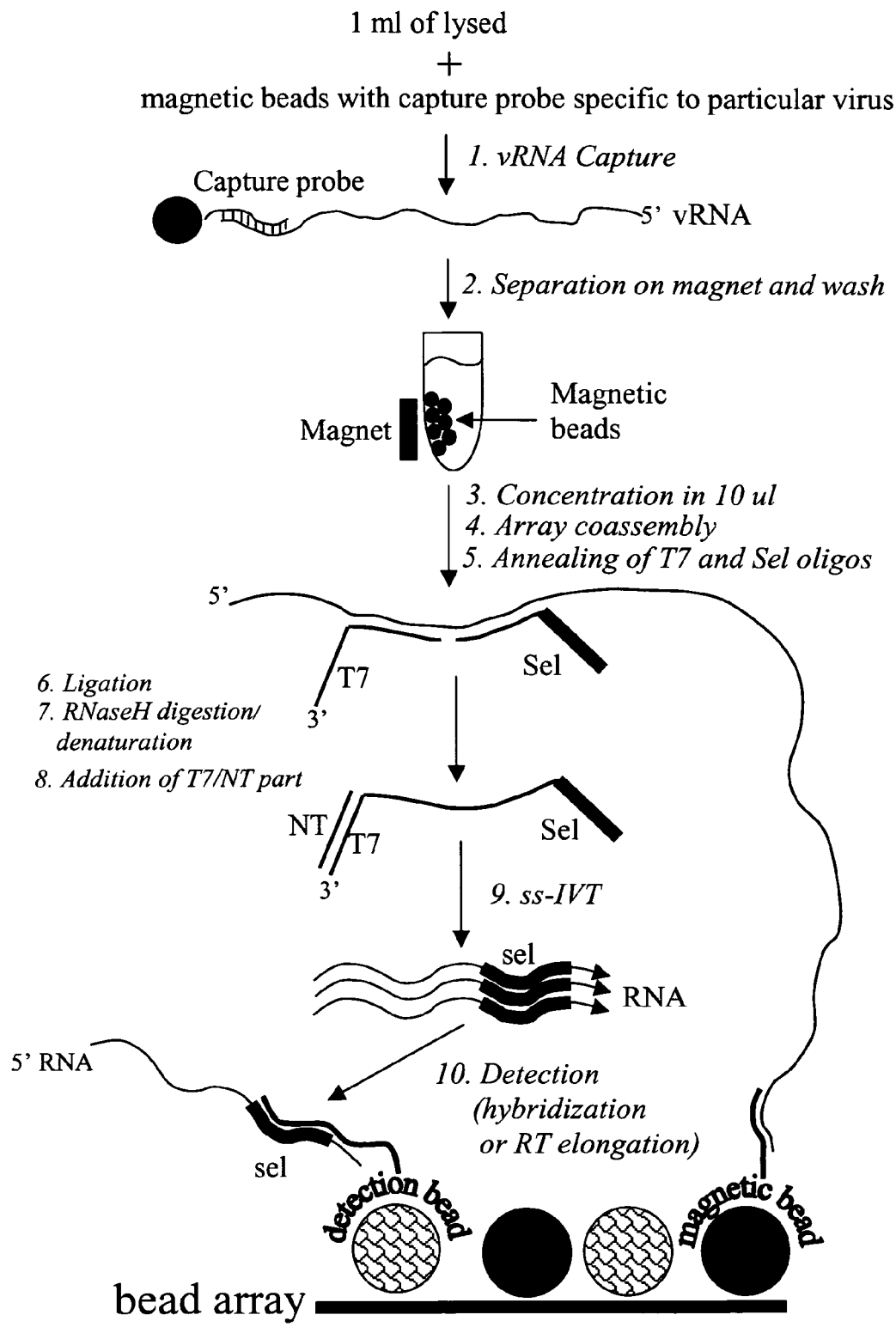
FIG. 18 shows a protocol for ligation-mediated RNA viral detection.

The comparative simplicity of the protocol permits the integration of additional steps, especially the capture of mRNA to magnetic particles in accordance with standard protocols (U.S. Pat. No. 5,759,820), with sst-IVT and multiplexed detection. As illustrated in FIG. 18 for ligation-mediated RNA analysis (here in particular—the detection of viral genomic RNA, see also supra), two constituents of the promoter-selector construct are permitted to anneal to matching subsequences of the captured mRNA (or viral RNA) strands, and—following ligation—amplification and concurrent detection on encoded beads is performed in a manner analogous to the co-assembled array format described above, without the need for removal of unused promoter. In fact, ligation, sst-IVT and RT-mediated probe elongation can be performed in the same buffer.

The use of magnetic particles for capture of target in solution, followed by co-assembly of an array of encoded microparticles, or the magnetic field-mediated deposition of the magnetic capture particles on an already assembled encoded bead array for product analysis, will permit the concentration of the original RNA strands in a small volume, in which the products of the subsequent sst-IVT amplification remain confined.

The methods and devices of the invention are further described and illustrated in the following Examples.

EXAMPLE I

Characterization of ssIVT Reaction: Dose Response and Time Course

Two different constructs, 64 and 62 nt in length, and respectively comprising RT priming sequences for IL-2R and IL-4I mRNAs, as well as the T7 promoter template strand, and a unique sel sequences, were used as a template for ss-IVT, with or without addition of the non-template strand of the T7-promoter. To elucidate the potential sensitivity of this approach, the concentrations of these primers were varied in the range of 100-0.1 fmol/10 μl rxn. Obtained RNA (by MEGAshortscript™ T7 kit, Ambion, cat# 1354) during 2 h of incubation at 37° C. was used for on-chip reverse transcription, followed by detection of the resulting signal on encoded beads which were functionalized with capture sequences matching the IL-2R and IL-4I selectors (FIG. 5). The time course for IVT reaction for IL-2R ssDNA has been done in the same manner (FIG. 6) with incubation times of 2, 4, 6, and 18 hours at 37° C.

EXAMPLE II

Assay Sensitivity Using Column Purification: Kanamycin mRNA

The first step in the assay is cDNA synthesis. The construct—RT primer consisting of RT/T7/Sel sequences, 64 nt in length, was designed to generate cDNA of ~500 nt in length. The reagents used were as follows:

Kanamycin mRNA—a positive control (Promega, Cat.# C1381)
Superscript™ III First-Strand Synthesis System (Invitrogen, Cat # 18080-051)
MEGAshortscript™ T7 kit (Ambion, Cat# 1354)
Cy3 labeled dCTP (Amersham, Cat# PA53021)
BAS BeadChip™ (BioArray Solutions, Ltd)
PCR purification kit (Qiagen, #28104)
All reactions were conducted in thermocycler.

To address the dose response the following dilutions of the mRNAs were prepared using RNase Out treated DEPC water (14 μl of 40 U/μl RNase out+266 μl of DEPC water): 1300, 100, 10, 1 to 0.1 fmol/ul.

cDNA synthesis was performed by assembling Mix1: 1 ul of 0.1 μM RT/T7/Sel construct, 1 ul of RNA (different concentrations), 2 μl of 5×FS Buffer, 6 μl of DEPC treated DIwater. Tubes were incubated at 65° C. for 5 minutes followed by 10 minutes of incubation at 4° C. During the incubation, the following Mix2 was added to each tube: 2 μl of 5×FS Buffer, 2 μl of 0.1 M DTT, 1 μl of 10 mM dNTP mix, 1 μl of Superscript III enzyme (200 U/μl), 4 μl of DEPC treated DIwater. The RT reaction was performed at 50° C. for 60 minutes and enzyme was deactivated at 85° C. for 5 minutes followed by 10 minutes of incubation at 4° C. 10 μl of final cDNA mix was purified on a column using a Qiagen PCR purification kit, according to manufacturer's instructions.

1 μl of purified cDNA was added to 10 μl of IVT mix containing 1 μl of each 75 mM NTPs, 1 μl of T7 10× Reaction Buffer, 1 μl of T7 Enzyme Mix, 1 μl of 0.1 μM NT portion for T7, 2 μl of DEPC treated DIwater, and incubated for 2 h at 37° C.

RNA products were detected by an on-chip reverse transcription labeling step as follows:

10 μl of resulted IVT reaction were mixed with 10 μl of RT mix: 1 ul of Superscript III enzyme (200 U/μl), 2 μl of 5×FS Buffer, 1 μl of 0.1M DTT, 2 μl of 10 μM dNTPs (no dCTP), 1 μl of 25 μM Cy3-dCTP, 3 μl of DEPC treated DIwater, and 20 μl of the product were placed on top of the assembled bead chip with detection beads containing probes for Sel sequence. The chip was incubated for 15 min at 50° C., washed 3× with 20 μl of DEPC treated DIwater and imaged. Results are shown in FIG. 7.

EXAMPLE III

Purification

Figure 8:
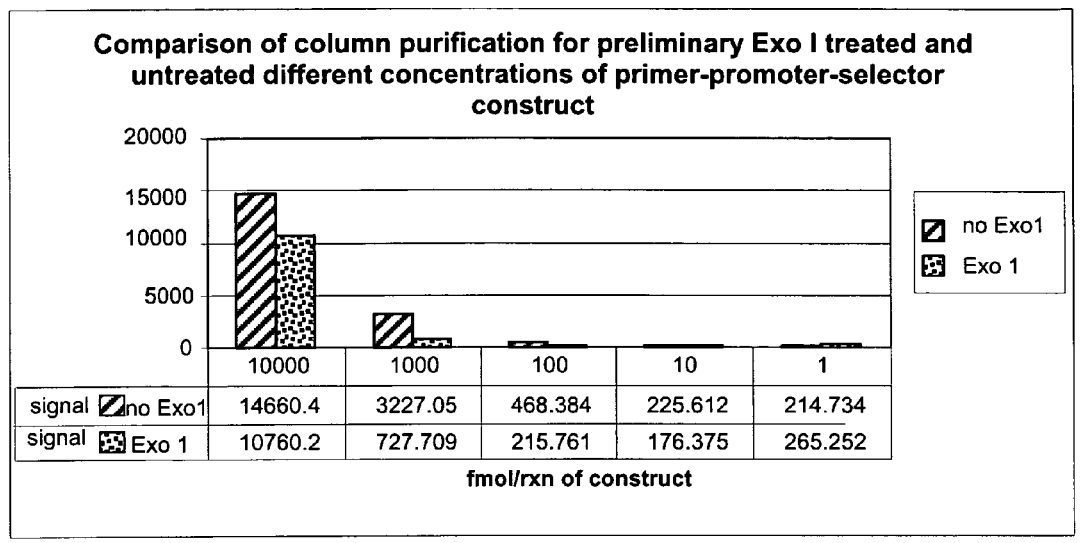
FIG. 8 shows efficiency of Exo I treatment followed by column purification for different concentrations of construct.

Experiments were performed to determine the range of optimal RT construct concentrations, by performing the reaction with different concentrations of construct using a combination of column purification and ExoI digestion. Specifically, the reaction mix was placed on a column (Qiagen, cat#28104), either with, or without prior ExoI treatment. Following column purification, 2 µl of eluate aliquot was used directly in the sst-IVT reaction, and the RNA products were detected by way of on-chip RT-mediated probe elongation (FIG. 8). Exo I treatment was performed in 10 µl of reaction mix consisting of 1 µl of construct (different concentrations), 1 ul of Exo I (New England Biolabs (NEB), Cat# M0293S), 2 µl of 5×FS buffer (see Example II) for 30 min at 37°C. followed by Exo I inactivation for 20 min at 80° C. FS buffer was used to reproduce the actual conditions of the Exo I treatment of the assay, though the optimal buffer conditions for digestion are provided by Exo I 10× buffer (NEB).

EXAMPLE IV

Eliminating RNaseH Digestion Step

The necessity of RNaseH digestion was first examined in a model system where it is assumed that the configuration of the annealed oligonucleotides to RNA resembles the configuration in actual assay. The construct was obtained as a result of the annealing of the RT/T7/Sel construct with IL-2R RNA of 50 nt long, with only the RT part of the construct being annealed to RNA. Following sst-IVT reaction, the product was detected on-chip by reverse transcription. Different conditions are shown in the legend to FIG. 10. RNaseH (1 µl of 2 U/µl, Invitrogen, Cat# 18021-014) digestion was performed at 37° C. for 20 minutes.

As a second step, the RHaseH digestion effect or absence thereof was checked in the whole assay (Example II) after a column purification step. To this purpose, 2 µl of 5×FS buffer, 2 µl of 0.1M DTT, and 1 µl of RNaseH was added to 10 µl of purified cDNA. In the control reaction with no RNaseH digestion, 4 µl of the elution buffer was added. The results are presented in FIG. 11.

EXAMPLE V

Solid Phase sst-IVT

This reaction, including controls, was performed for one particular concentration of the construct. 1 µl of ssDNA RT/T7/Sel IL-2R biotinylated at 3'-end at the 100 fmol/µl was added to 10 µl of magnetic beads (0.2 µm nanoparticles, Molecular probes, Cat# C-21476), incubated for 15 min and followed by extensive washing with 10 mM Tris HCl pH 8. Final volume was adjusted to 10 µl with construct concentration to be 10 fmol/µl of beads (FIG. 12, line 1). The 10 µl of IVT mix (see Example II) was added to the immobilized construct and the reaction mix was incubated for 2 h at 37° C. Products were detected by the RT eMAP method. Line 2 represents the same set up lacking the washing step, and the line 3 represents the same experiment with no magnetic beads present, i.e. IVT reaction in solution. In all three cases the construct concentration was adjusted to 10 fmol/µl.

EXAMPLE VI

Discrimination of Closely Homologous mRNA Sequences: Inbred Strains of Maize Certain applications call for the detection of specific targets within an ensemble of hundreds or thousands of targets displaying substantial sequence homology with the target(s) of interest. These applications generally require a degree of sequence-specificity beyond that afforded by hybridization-mediated analysis. Two designs described above were used to detect closely homologous members of mRNA sequences in the Maize zein gene family. In the two inbred maize lines B73 and BSSS53, certain mRNA sequences of the zein genes display a degree of 95% to 99% homology over the entire 945 nt of the sequence. The task of detecting these sequences and estimating their respective expression levels with current methods is a very laborious process, requiring sequencing of large sets of clones.

Thus the combinations of sequence-specific elongation by reverse transcriptase or ligation at the site of polymorphism, followed with sst-IVT amplification of distinct "selector" sequences, will be aid in discriminating between highly homologous sequences of mRNAs, while simultaneously determining respective abundances of these messages in a highly parallel format of analysis.

FIG. 14 illustrates the positions of the polymorphic sites and thus possible sites for ligation or placement of 3'-end of the construct. For some complicated cases of sequence discrimination, involving two sequences having a common mutation, but only one having a second specific mutation (for example, genes 16 and 31 have the same mutation T/G, that discriminates them from the all other sequences in a multiple sequence alignment, but gene 31 has a unique mutation C/G) the described methods above have the advantage of assigning of particular selector sequence to each proximal polymorphic site.

EXAMPLE VII

Concurrent on-chip Amplification/Detection Reaction

DNA, containing the T7 promoter and a transcribed sequence of 28 nt (equivalent to the 5'-end of Kan mRNA), and biotinylated at the 3'-end of the non-template (NT) strand, was applied at different concentrations to BeadChips, and following an initial 10 min incubation to permit capture, residual free DNA was removed by washing. 20 µl of reagent mixture for the concurrent IVT/RT reaction was then applied on the surface of the chip. The reaction mixture contained: 2 µl of each 75 mM NTPs, 2 µl of T7 10× Reaction Buffer, 2 µl of T7 Enzyme Mix, 2 µl of 0.1 µM NT portion for T7 promoter, 2 µl of 10 µM dNTP mix (without dCTP), 1 µl of 25 µM Cy3 dCTP, 1 µl of Superscript III enzyme (200 U/µl), and 2 µl of DEPC treated DIwater. The reaction was performed on-chip in a humidified chamber and involved incubation at 37° C. for 1 h (IVT), followed by incubation at 50° C. for 15 minutes (RT-mediated probe elongation). The results and the scheme of experiments are shown in FIG. 17 and FIG. 16, accordingly.

It should be understood that the terms, expressions and examples used herein are exemplary only, and not limiting, and that the scope of the invention is defined only in the claims which follow, and includes all equivalents of the subject matter of the claims. Process and method steps in the claims can be carried out in any order, including the order set forth in the claims, unless otherwise specified in the claims.

What is claimed is:

1. A primer-promoter-selector nucleic acid construct for detecting the presence or the relative quantity of a target subsequence in a sample, comprising three subsequences including:
   a target specific primer subsequence complementary to said target subsequence, having its 5' end adjacent to the 3' end of a promoter subsequence, said promoter subsequence oriented to direct transcription of a selector subsequence, said selector sequence having its 3' end adjacent to the 5' end of the promoter subsequence, wherein the selector subsequence and its complementary sequence do not anneal any subsequences present in the sample and wherein said selector subsequence serves as a template for single stranded in vitro transcription.

2. The construct of claim 1 wherein the promoter is a T7 or T3 or SP6 promoter subsequence.

3. The construct of claim 1 including an identifiable label.

4. A kit comprising a plurality of different types of primer-promoter-selector nucleic acid constructs each for detecting the presence or relative quantity of a different target subsequence in a sample, each comprising three subsequences including:
   a target specific primer subsequence complementary to said target subsequence, having its 5' end adjacent to the 3' end of a promoter subsequence, said promoter subsequence oriented to direct transcription of a selector subsequence, said selector sequence having its 3' end adjacent to the 5' end of the promoter subsequence, wherein the selector subsequence and its complementary sequence do not anneal to any subsequences present in the sample and wherein said selector subsequence serves as a template for single stranded in vitro transcription; and
   a set of oligonucleotides, wherein oligonucleotides with different sequences are displayed on differently-encoded microparticles, and wherein the oligonucleotides are capable of annealing to the transcription product of the selector subsequence.

5. The kit of claim 4 wherein the different types of constructs differ in their respective primer subsequence and selector subsequences.

6. The kit of claim 5 wherein each type of construct has different primer subsequence and the same selector subsequences.

7. The kit of claim 4 further including labeled NTPs capable of being incorporated into the transcription product.

8. The kit of claim 7 wherein the NTPs are optically labeled.

9. The kit of claim 4 wherein the promoter is a T7 or T3 or SP6 promoter subsequence template strand.

10. The kit of claim 9 further including a nontemplate T7, T3 or SP6 promoter subsequence capable of forming a duplex with said T7, T3 or SP6 promoter subsequence.

11. The kit of claim 4 further including a set of differently-encoded microparticles adapted for attaching different types of oligonucleotides thereto which are complementary to the transcription products.

12. The kit of claim 4 further including a set of labeled ddNTPs or dNTPs designed for incorporation into an extension product when the primer subsequence is extended.

13. The kit of claim 4 further including hapten labeled ddNTPs or dNTPs.

14. The kit of claim 13 further including magnetic particles.

15. The kit of claim 4 further including an oligonucleotide capable of annealing to a subsequence in the sample which is located to the 3' side of a primer's targeted subsequence or to the primer.

16. The kit of claim 15 wherein the oligonucleotide is labeled.

17. The kit of claim 15 wherein the oligonucleotide includes the promoter subsequence.

* * * * *

UNITED STATES PATENT AND TRADEMARK OFFICE
CERTIFICATE OF CORRECTION

PATENT NO. : 8,206,953 B2
APPLICATION NO. : 11/525064
DATED : June 26, 2012
INVENTOR(S) : Nataliya Korzheva et al.

Page 1 of 1

It is certified that error appears in the above-identified patent and that said Letters Patent is hereby corrected as shown below:

In the Claims:

In the ninth line of claim 1, at line 41 of column 25, please delete "selector sequence" and insert therefor --selector subsequence--.

In the tenth line of claim 4, at line 58 of column 25, please delete "selector sequence" and insert therefor --selector subsequence--.

In the second line of claim 5, at line 33 of column 26, please delete "subsequence".

In the second line of claim 6, at line 36 of column 26, please delete "subsequence" and insert therefor --subsequences--.

Signed and Sealed this
Fifteenth Day of October, 2013

Teresa Stanek Rea
*Deputy Director of the United States Patent and Trademark Office*